US012670549B2

(12) United States Patent
Graetzel et al.

(10) Patent No.: US 12,670,549 B2
(45) Date of Patent: Jun. 30, 2026

(54) VISUALIZATION ADJUSTMENTS FOR INSTRUMENT ROLL

(71) Applicant: Auris Health, Inc., Santa Clara, CA (US)

(72) Inventors: Chauncey F. Graetzel, Palo Alto, CA (US); Rachel Leigh Chok, Sunnyvale, CA (US); Claire Elizabeth Kingston, San Francisco, CA (US); Sarah Plewe, Redwood City, CA (US); Jason J. Hsu, Mountain View, CA (US)

(73) Assignee: Auris Health, Inc., Santa Clara, CA (US)

( * ) Notice: Subject to any disclaimer, the term of this patent is extended or adjusted under 35 U.S.C. 154(b) by 332 days.

(21) Appl. No.: 18/316,083

(22) Filed: May 11, 2023

(65) Prior Publication Data

US 2024/0127399 A1    Apr. 18, 2024

Related U.S. Application Data

(63) Continuation of application No. PCT/IB2021/060929, filed on Nov. 24, 2021.

(Continued)

(51) Int. Cl.
*A61B 1/00* (2006.01)
*A61B 1/018* (2006.01)
*G06T 3/60* (2006.01)

(52) U.S. Cl.
CPC ............ *G06T 3/60* (2013.01); *A61B 1/00006* (2013.01); *A61B 1/00039* (2013.01);
(Continued)

(58) Field of Classification Search
CPC ... G06T 3/60; A61B 1/00006; A61B 1/00039; A61B 1/0005; A61B 1/00149;
(Continued)

(56) References Cited

U.S. PATENT DOCUMENTS 8,102,416 B2    1/2012   Ito et al.
10,362,240 B2    7/2019   Richardson et al.
(Continued)

FOREIGN PATENT DOCUMENTS

CN    102740755 A    10/2012
CN    105188511 A    12/2015
(Continued)

OTHER PUBLICATIONS

Office Action, dated May 20, 2025, from Japan Patent Application No. 2023-531010, 13 pages.
(Continued)

*Primary Examiner* — Anh Tuan T Nguyen
*Assistant Examiner* — James Edward Boice
(74) *Attorney, Agent, or Firm* — Paradice & Li LLP

(57) ABSTRACT

Techniques relate to providing image data, indicators, and/or other data associated with a medical instrument with the appropriate orientation to assist a user in performing a procedure. For example, a user interface can present an image representation representing image data from a scope and/or a working channel indicator indicating an angle of rotation of a working channel of the scope. When the scope rolls, a rotation adjustment can be applied to the image representation to rotate the image representation within the user interface. Further, the working channel indicator can rotate within the user interface.

19 Claims, 10 Drawing Sheets

Related U.S. Application Data

(60) Provisional application No. 63/117,658, filed on Nov. 24, 2020.

(52) U.S. Cl.
CPC ........ *A61B 1/0005* (2013.01); *A61B 1/00149* (2013.01); *A61B 1/018* (2013.01)

(58) Field of Classification Search
CPC .............. A61B 1/018; A61B 1/000095; A61B 1/00009; A61B 1/05; A61B 1/00045
USPC .......................................... 600/104; 604/264
See application file for complete search history.

(56)                    References Cited

U.S. PATENT DOCUMENTS

| | | | |
|---|---|---|---|
| 10,918,264 | B2 | 2/2021 | Dejima et al. |
| 2002/0188172 | A1 | 12/2002 | Irion et al. |
| 2010/0324364 | A1 | 12/2010 | Sasaki |
| 2014/0357947 | A1 | 12/2014 | Fujitani |
| 2017/0188792 | A1* | 7/2017 | Itkowitz ............... A61B 1/0005 |
| 2019/0183321 | A1* | 6/2019 | Teranuma ............ H04N 23/555 |
| 2019/0192244 | A1* | 6/2019 | Mirbagheri ............ B25J 9/1689 |
| 2019/0246873 | A1 | 8/2019 | Lu et al. |
| 2019/0290371 | A1* | 9/2019 | Calef ..................... A61B 34/30 |
| 2020/0015899 | A1 | 1/2020 | Scheib et al. |
| 2021/0127949 | A1* | 5/2021 | Tata ................... A61B 1/00006 |

FOREIGN PATENT DOCUMENTS

| | | | |
|---|---|---|---|
| CN | 106102549 | A | 11/2016 |
| CN | 110151100 | A | 8/2019 |
| EP | 2997879 | A1 | 3/2016 |
| EP | 2997879 | B1 | 3/2019 |
| JP | 2005-287832 | A | 10/2005 |
| JP | 4728456 | B1 | 7/2011 |
| KR | 101500717 | B1 | 3/2015 |
| WO | 2015142957 | A1 | 9/2015 |
| WO | 2017119401 | A1 | 7/2017 |

OTHER PUBLICATIONS

Supplementary European Search Report, issued on Aug. 29, 2024, in European Patent Application No. 21897284.2, 8 pages.
International Search Report for appl No. PCT/IB2021/060929, dated Mar. 2, 2022, 4 pages.
Written Opinion for appl No. PCT/IB2021/0609229, dated Mar. 2, 2022, 5 pages.
Examination Report, issued on Dec. 19, 2025, in European Patent Application No. 21897284.2, 4 pages.
Office Action, dated Nov. 7, 2025, from Japan Patent Application No. 2023-531010, 6 pages.
Office Action from China Patent Application No. 202180079014.5, dated Mar. 28, 2026, 15 pages.

* cited by examiner

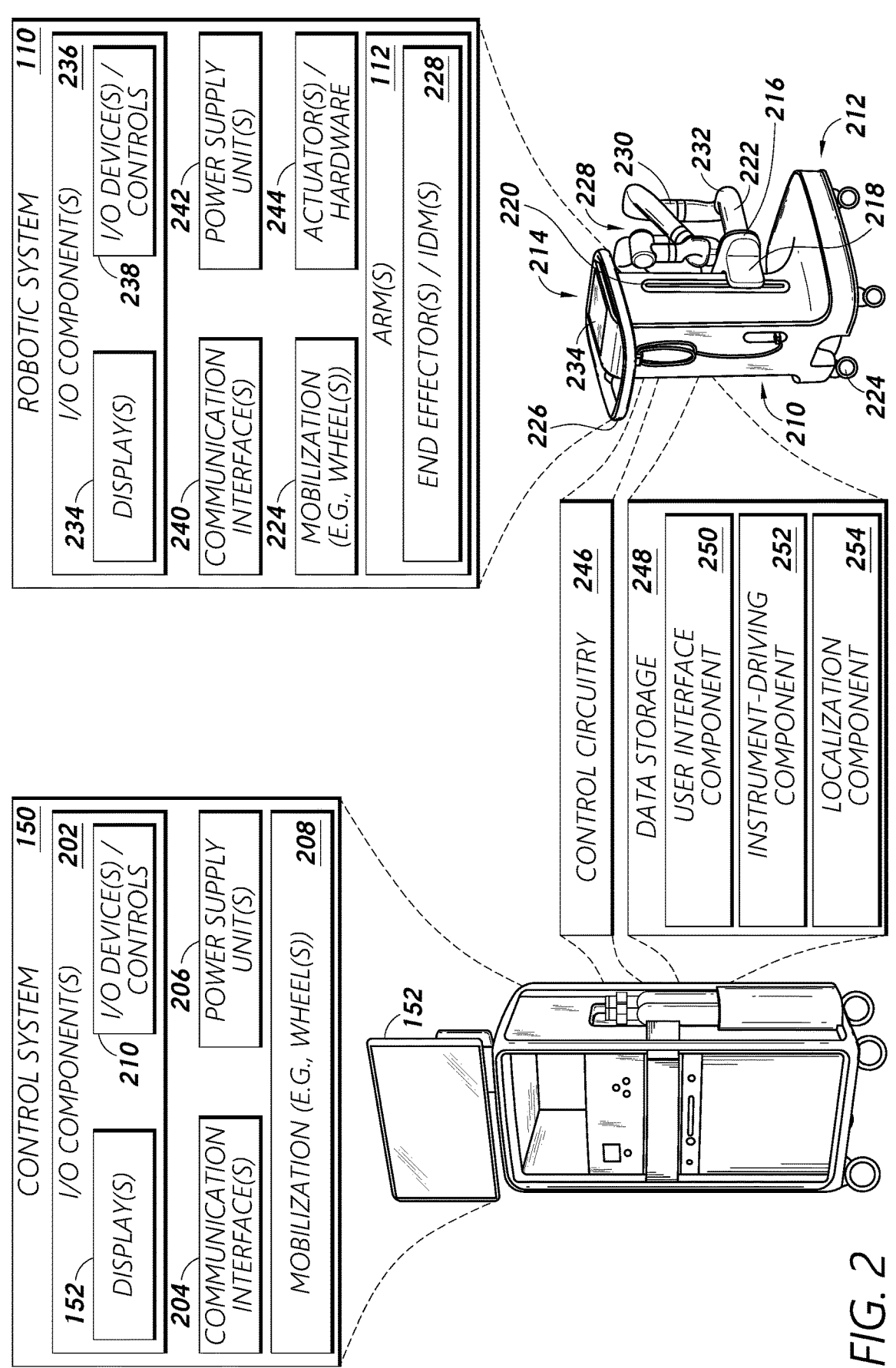

ROBOTIC SYSTEM _110_

I/O COMPONENT(S) _236_
- DISPLAY(S) _234_
- I/O DEVICE(S) / CONTROLS _238_

POWER SUPPLY UNIT(S) _242_

COMMUNICATION INTERFACE(S) _240_

ACTUATOR(S) / HARDWARE _244_

MOBILIZATION (E.G., WHEEL(S)) _224_

ARM(S) _112_

END EFFECTOR(S) / IDM(S) _228_

CONTROL SYSTEM _150_

I/O COMPONENT(S) _202_
- DISPLAY(S) _152_
- I/O DEVICE(S) / CONTROLS _210_

POWER SUPPLY UNIT(S) _206_

COMMUNICATION INTERFACE(S) _204_

MOBILIZATION (E.G., WHEEL(S)) _208_

CONTROL CIRCUITRY _246_

DATA STORAGE _248_

USER INTERFACE COMPONENT _250_

INSTRUMENT-DRIVING COMPONENT _252_

LOCALIZATION COMPONENT _254_

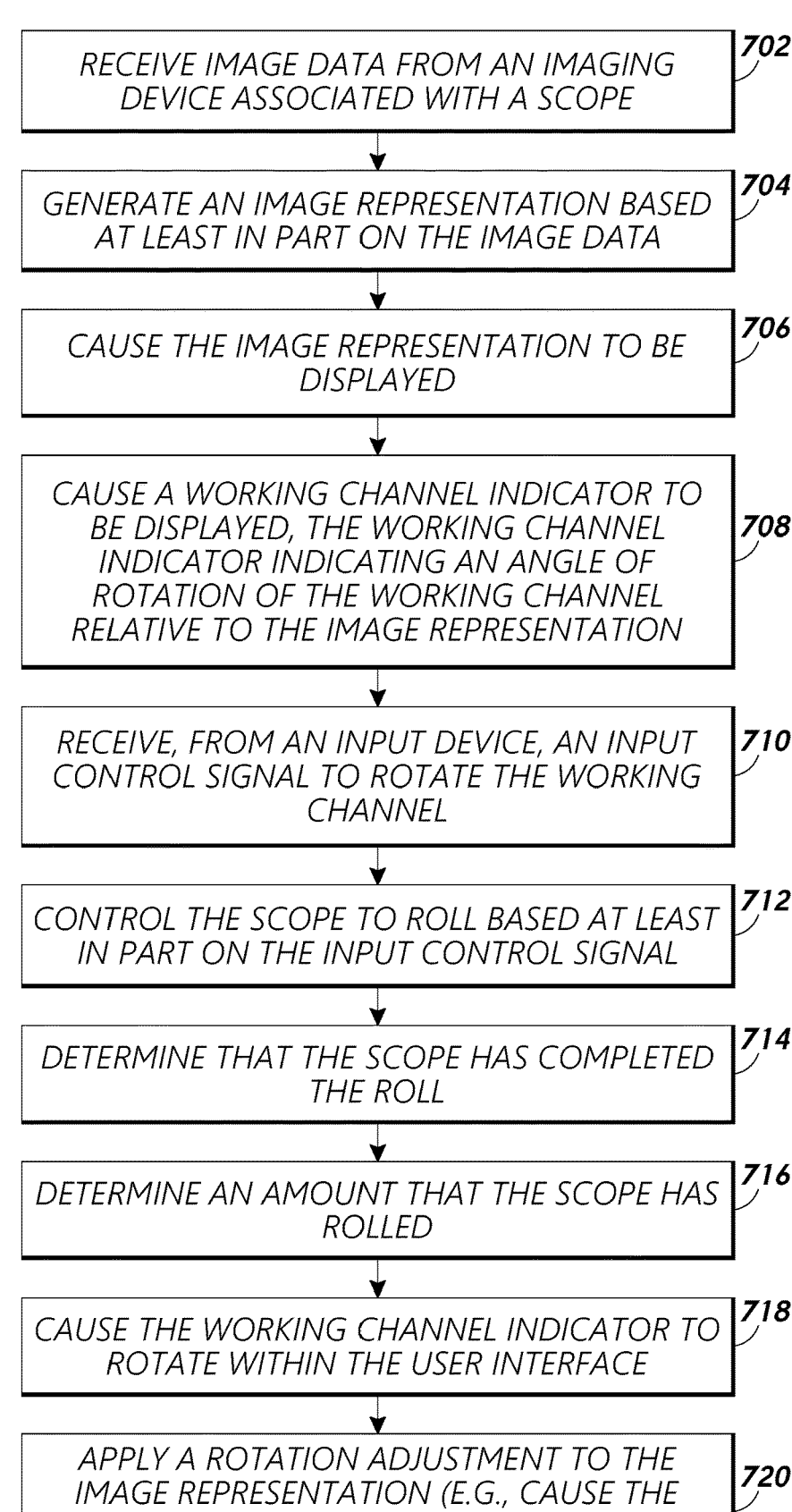

700

| RECEIVE IMAGE DATA FROM AN IMAGING DEVICE ASSOCIATED WITH A SCOPE | 702 |

| GENERATE AN IMAGE REPRESENTATION BASED AT LEAST IN PART ON THE IMAGE DATA | 704 |

| CAUSE THE IMAGE REPRESENTATION TO BE DISPLAYED | 706 |

| CAUSE A WORKING CHANNEL INDICATOR TO BE DISPLAYED, THE WORKING CHANNEL INDICATOR INDICATING AN ANGLE OF ROTATION OF THE WORKING CHANNEL RELATIVE TO THE IMAGE REPRESENTATION | 708 |

| RECEIVE, FROM AN INPUT DEVICE, AN INPUT CONTROL SIGNAL TO ROTATE THE WORKING CHANNEL | 710 |

| CONTROL THE SCOPE TO ROLL BASED AT LEAST IN PART ON THE INPUT CONTROL SIGNAL | 712 |

| DETERMINE THAT THE SCOPE HAS COMPLETED THE ROLL | 714 |

| DETERMINE AN AMOUNT THAT THE SCOPE HAS ROLLED | 716 |

| CAUSE THE WORKING CHANNEL INDICATOR TO ROTATE WITHIN THE USER INTERFACE | 718 |

| APPLY A ROTATION ADJUSTMENT TO THE IMAGE REPRESENTATION (E.G., CAUSE THE IMAGE REPRESENTATION TO ROTATE WITHIN THE USER INTERFACE) | 720 |

FIG. 7

VISUALIZATION ADJUSTMENTS FOR INSTRUMENT ROLL

RELATED APPLICATION(S)

This application is a continuation of International Application No. PCT/IB2021/060929, filed on Nov. 24, 2021, and entitled VISUALIZATION ADJUSTMENTS FOR INSTRUMENT ROLL, which claims priority to U.S. Provisional Application No. 63/117,658, filed Nov. 24, 2020, and entitled VISUALIZATION ADJUSTMENTS FOR INSTRUMENT ROLL, the disclosures of which are hereby incorporated by reference in their entirety.

BACKGROUND

Various medical procedures involve the use of one or more medical instruments to investigate and/or treat patients. In some cases, multiple systems/devices are implemented to control a medical instrument to perform a procedure on a patient. The improper use of such systems, devices, and/or medical instruments can adversely affect the health of the patient and/or efficacy of the procedure.

SUMMARY

In some implementations, the present disclosure relates to a control system comprising a communication interface configured to receive image data from an imaging device associated with a scope that includes a working channel to deploy a medical instrument, and control circuitry communicatively coupled to the communication interface. The control circuitry is configured to generate an image representation of the image data, display the image representation in the user interface, determine an amount that the scope has rolled, and based at least in part on the amount that the scope has rolled, cause the image representation to rotate within the user interface.

In some embodiments, the control circuitry is configured to display a working channel indicator in the user interface, and based at least in part on the amount that the scope has rolled, cause the working channel indicator to rotate within the user interface from a first orientation relative to the user interface to a second orientation relative to the user interface. The working channel indicator can indicate an angle of rotation of the working channel relative to the image representation. Further, in some embodiments, the control circuitry is configured to display the working channel indicator by overlaying the working channel indicator on the image representation.

In some embodiments, the control circuitry is configured to determine that the scope has completed the roll, and in response to determining that the scope has completed the roll, cause the image representation to rotate within the user interface. Further, in some embodiments, the control circuitry is configured to cause the image representation to rotate within the user interface as the scope rolls.

In some embodiments, the control circuitry is configured to cause the image representation to rotate within the user interface by displaying the image representation in a cropped form in the user interface while rolling the scope.

In some embodiments, the control circuitry is configured to determine the amount that the scope has rolled based on at least one of feedback data from a robotic arm configured to couple to the scope, sensor data generated by a position sensor associated with the scope, or a control signal generated to control the robotic arm.

In some embodiments, the control circuitry is configured to receive, from an input device, an input control signal to rotate the working channel, and control the scope to roll based at least in part on the input control signal. The control circuitry can be configured to control the scope to roll by controlling the scope to roll a predetermined amount.

In some implementations, the present disclosure relates a method comprising receiving image data from an imaging device associated with a scope, displaying, by control circuitry, an image representation of the image data in a user interface, displaying, by the control circuitry, a working channel indicator in the user interface, determining an amount that the scope has rolled, and based at least in part on the amount that the scope has rolled: rotating the image representation within the user interface, and rotating the working channel indicator within the user interface from a first orientation to a second orientation. The scope includes a working channel. Further, the working channel indicator indicates an angle of rotation of the working channel relative to the image representation.

In some embodiments, the method further comprises determining that the scope has completed the roll. The rotating the image representation and the rotating the working channel indicator can occur in response to the determining that the scope has completed the roll.

In some embodiments, the rotating the image representation includes rotating the image representation in a continuous manner. Further, in some embodiments, the determining the amount that the scope has rolled is based on at least one of feedback data from a robotic arm configured to couple to the scope, position data generated by a position sensor associated with the scope, or a control signal generated to control the robotic arm. Moreover, in some embodiments, the rotating the image representation includes displaying the image representation in a cropped form in the user interface while rolling the scope.

In some embodiments, the method further comprises receiving, from an input device, user input to rotate the scope by a predetermined amount, and controlling the scope to roll the predetermined amount. Further, in some embodiments, the displaying the working channel indicator includes overlaying the working channel indicator on the image representation.

In some implementations, the present disclosure relates a system comprising a scope that includes a working channel to removably receive a medical instrument, an imaging device configured to couple to the scope, and control circuitry communicatively coupled to the scope and the imaging device. The control circuitry is configured to receive image data from the imaging device, cause an image representation of the image data to be displayed in a user interface, cause a working channel indicator to be displayed in the user interface, determine an amount that the scope has rolled, based at least in part on the amount that the scope has rolled, rotate the working channel indicator in the user interface, and based at least in part on the amount that the scope has rolled, apply a rotation adjustment to the image representation in the user interface. The working channel indicator indicates an angle of rotation of the working channel.

In some embodiments, the working channel is offset from a longitudinal axis of the scope. Further, in some embodiments, the control circuitry is configured to control the scope to roll in a rotation direction, and apply the rotation adjustment to the image representation by causing the image representation to rotate within the user interface in the rotation direction.

In some embodiments, the control circuitry is further configured to determine that the scope has completed the roll. The rotation adjustment can be applied in response to determining that the scope has completed the roll. Further, in some embodiments, the control circuitry is configured to apply the rotation adjustment by rotating the image representation in a continuous manner as the scope rolls.

In some embodiments, the control circuitry is further configured to determine the amount that the scope has rolled based on at least one of feedback data from a robotic arm configured to couple to the scope, sensor data generated by a position sensor associated with the scope, or a control signal generated to control the robotic arm.

In some embodiments, the control circuitry is configured to apply the rotation adjustment by displaying the image representation in a cropped form in the user interface while rolling the scope. Further, in some embodiments, the control circuitry is configured to receive an input control signal to rotate the working channel, and control the scope to roll based at least in part on the input control signal.

In some implementations, the present disclosure relates one or more non-transitory computer-readable media storing computer-executable instructions that, when executed by control circuitry, cause the control circuitry to perform operations comprising receiving image data from an imaging device associated with a scope, displaying an image representation of the image data in a user interface, displaying a working channel indicator in the user interface, determining an amount that the scope has rolled, based at least in part on the amount that the scope has rolled, rotating the image representation within the user interface, and based at least in part on the amount that the scope has rolled, rotating the working channel indicator within the user interface from a first orientation to a second orientation. The scope includes a working channel. The working channel indicator indicates an angle of rotation of the working channel.

In some embodiments, the operations further comprise determining that the scope has completed the roll. The image representation and the working channel indicator can be rotated in response to the determining that the scope has completed the roll. Further, in some embodiments, the rotating the image representation includes rotating the image representation in a continuous manner.

In some embodiments, the determining the amount that the scope has rolled includes tracking an amount of roll of the scope based on at least one of feedback data from a robotic arm configured to couple to the scope, sensor data generated by a position sensor associated with the scope, or a control signal generated to control the robotic arm. Further, in some embodiments, the rotating the image representation includes displaying the image representation in a cropped form in the user interface while rolling the scope.

In some embodiments, the operations further comprise receiving, from an input device, user input to rotate the scope by a predetermined amount, and controlling the scope to roll the predetermined amount. Further, in some embodiments, the working channel indicator is displayed in an overlaid manner on the image representation.

For purposes of summarizing the disclosure, certain aspects, advantages and features have been described. It is to be understood that not necessarily all such advantages may be achieved in accordance with any particular embodiment. Thus, the disclosed embodiments may be carried out in a manner that achieves or optimizes one advantage or group of advantages as taught herein without necessarily achieving other advantages as may be taught or suggested herein.

BRIEF DESCRIPTION OF THE DRAWINGS

Various embodiments are depicted in the accompanying drawings for illustrative purposes and should in no way be interpreted as limiting the scope of the disclosure. In addition, various features of different disclosed embodiments can be combined to form additional embodiments, which are part of this disclosure. Throughout the drawings, reference numbers may be reused to indicate correspondence between reference elements.

FIG. 2 illustrates example details of the control system and the robotic system of FIG. 1 in accordance with one or more embodiments.

FIGS. 4-1 through 4-9 illustrate an example of rolling a scope and applying a rotation adjustment to a scope image within a user interface when the scope has completed the roll in accordance with one or more embodiments.

FIGS. 5-1 through 5-5 illustrate an example of rolling a scope and applying a rotation adjustment to a scope image within a user interface while the scope rolls in accordance with one or more embodiments.

FIG. 6 illustrates an example user interface to assist a user in controlling a scope and/or an instrument deployed through a working channel of the scope in accordance with one or more embodiments.

FIG. 7 illustrates an example flow diagram of a process for applying a rotation adjustment to a scope view within a user interface in accordance with one or more embodiments.

DETAILED DESCRIPTION

Figure 1:
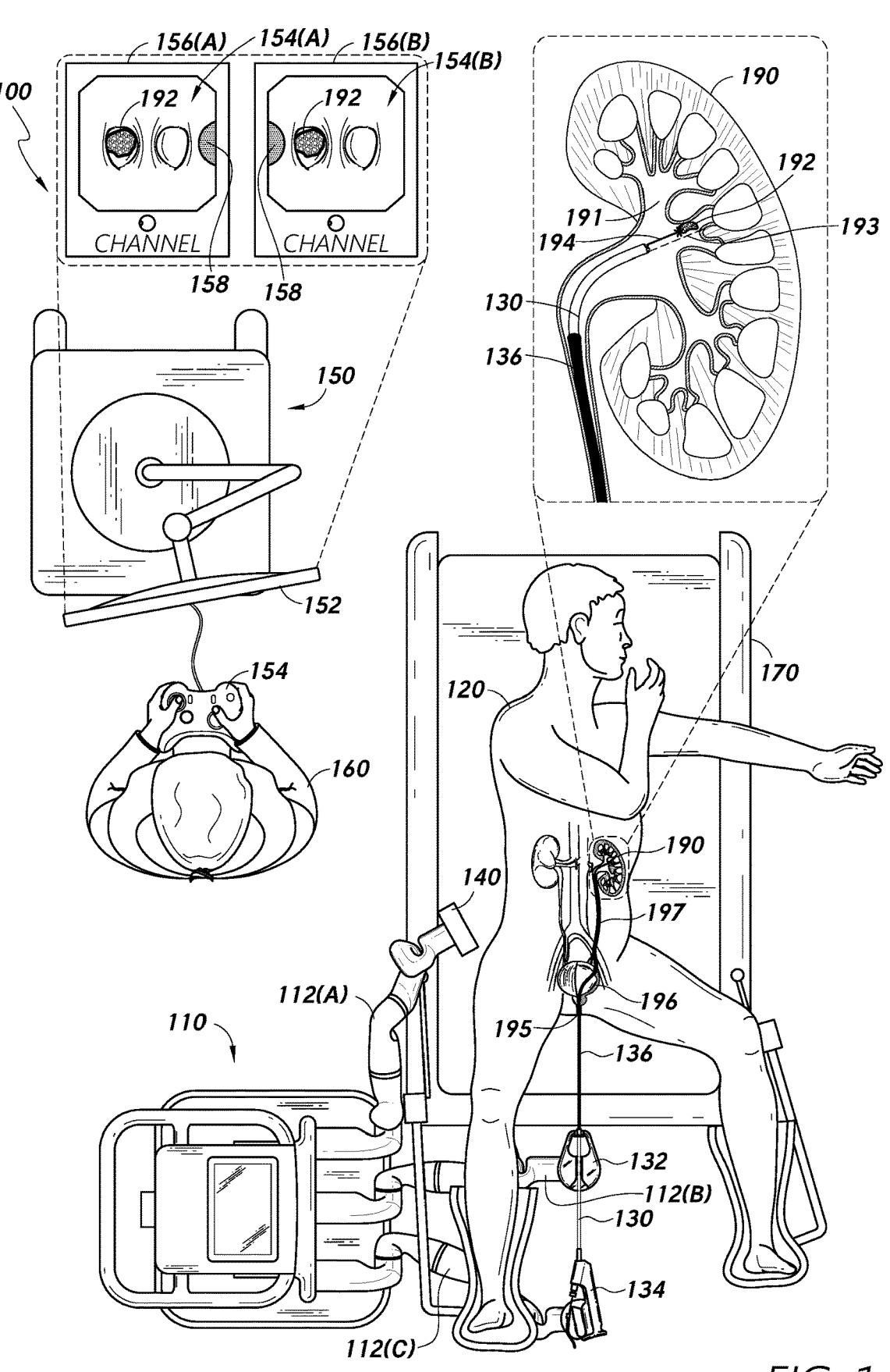
FIG. 1 illustrates an example medical system for performing various medical procedures in accordance with one or more embodiments.

The headings provided herein are for convenience only and do not necessarily affect the scope or meaning of the disclosure. Although certain embodiments and examples are disclosed below, subject matter extends beyond the specifically disclosed embodiments to other alternative embodiments and/or uses and to modifications and equivalents thereof. Thus, the scope of the claims that may arise here from is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Certain standard anatomical terms of location can be used herein to refer to the anatomy of animals, and namely humans, with respect to the preferred embodiments. Although certain spatially relative terms, such as "outer," "inner," "upper," "lower," "below," "above," "vertical," "horizontal," "top," "bottom," and similar terms, are used herein to describe a spatial relationship of one device/ element or anatomical structure to another device/element or anatomical structure, it is understood that these terms are used herein for ease of description to describe the positional relationship between element(s)/structures(s), as illustrated in the drawings. It should be understood that spatially relative terms are intended to encompass different orientations of the element(s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa.

OVERVIEW

Many medical procedures involve the use of a scope to investigate and/or treat a patient. A scope can generally include or be associated with an imaging device configured to capture image data of the target site, such as a camera at a distal end of the scope. The image data can be displayed to a user to assist the user in controlling the scope within the patient. A scope can also include one or more working channels through which additional tools, such as litho-tripters, basketing devices, forceps, laser devices, etc. can be deployed into the target site. A working channel is often offset from an imaging device and/or a longitudinal axis of the scope. Further, in some cases, a scope can be configured to move based on different articulation planes, such that the scope moves with more/less freedom in a direction when oriented in a particular manner.

To accommodate various scope movement, treatment angles, physician preferences, and/or other situations, a scope can be controlled to roll within the patient, causing an associated imaging device and working channel to roll. In one example, a user may roll a scope so that a tool/ instrument deployed through a working channel (which is offset to one side of the scope) has a more optimal position to treat a target site. In another example, a user may roll a scope to reorient an articulation plane of the scope to facilitate additional movement of the scope in a direction. Since a user is often controlling a scope based on image data captured by the scope, rolling the scope can cause the user to become disoriented within the patient. For instance, the image data displayed to the user will roll as the scope rolls, causing the user to lose track of a virtual horizon/frame of reference at the treatment site.

The present disclosure relates to systems, devices, and methods to provide image data and/or other data associated with a medical instrument with the suitable orientation to assist a user in performing a procedure. For example, a system can be configured to communicate with a scope that includes a working channel for deploying a medical instrument. The system can receive image data from an imaging device associated with the scope and display an image representation of the image data via a user interface. When the scope rolls, the system can adjust the orientation of the image representation, such as by rotating the image representation within the user interface, which may or may not be perceived as occurring in the user interface. The system can also display a working channel indicator via the user interface, which indicates an angle of rotation of the working channel (e.g., a position of the working channel relative to the image representation). The system can adjust the orientation of the working channel indicator within the user interface (e.g., rotate the working channel indicator) as the scope rolls to indicate an accurate orientation of the working channel relative to the image representation. In some instances, the image representation and/or the working channel indicator are adjusted in the user interface in a continuous manner while the scope rolls to give the perception that a virtual horizon/frame of reference (as displayed within the image representation) is maintained. For example, a user may perceive that just the working channel indicator moves within the user interface (e.g., the working channel indicator rotates while a virtual horizon within the image representation stays the same). In other instances, the image representation and/or the working channel indicator are rotated within the user interface when the scope has completed a roll or otherwise reached a particular rotation angle and/or when another event occurs. As such, the techniques can present image data, an indicator for a working channel, and/or other data associated with a scope with the appropriate orientation to assist a user in maintaining a frame of reference within the patient.

Although many techniques are discussed in the context of presenting a working channel indicator for a medical instrument, the techniques can additionally, or alternatively, present indicators for other elements. For example, the techniques can present an indicator for an articulation plane associated with a medical instrument, a light associated with the medical instrument, a needle/catheter/other instrument that is rendezvousing with the medical instrument, and so on.

In some implementations, the techniques discussed herein implement robotic-assisted medical procedures, wherein robotic tools enable a physician to perform endoscopic and/or percutaneous access and/or treatment for a target anatomical site. For example, the robotic tools can engage with and/or control one or more medical instruments, such as a scope, to access a target site in a patient and/or perform a treatment at the target site. In some cases, the robotic tools are guided/controlled by a physician. In other cases, the robotic tools operate in an automatic or semi-automatic manner. Although many techniques are discussed in the context of robotic-assisted medical procedures, the techniques may be applicable to other types of medical procedures, such as procedures that do not implement robotic tools or implement robotic tools for relatively few operations (e.g., less than a threshold number). For example, the techniques can be applicable to procedures in which a manually operated medical instrument is implemented, such as a manual scope controlled entirely by a physician.

Certain aspects of the present disclosure are described herein in the context of renal, urological, and/or nephrological procedures, such as kidney stone removal/treatment procedures. However, it should be understood that such context is provided for convenience, and the concepts disclosed herein are applicable to any suitable medical procedure. For example, the following description is also applicable to other surgical/medical operations or medical procedures concerned with the removal of objects from a patient, including any object that can be removed from a treatment site or patient cavity (e.g., the esophagus, ureter, intestine, eye, etc.) via percutaneous and/or endoscopic access, such as, for example, gallbladder stone removal, lung (pulmonary/transthoracic) tumor biopsy, or cataract removal. However, as mentioned, description of the renal/ urinary anatomy and associated medical issues and procedures is presented below to aid in the description of the concepts disclosed herein.

Example Medical System

FIG. 1 illustrates an example medical system 100 for performing various medical procedures in accordance with aspects of the present disclosure. The medical system 100 includes a robotic system 110 configured to engage with and/or control one or more medical instruments/devices to perform a procedure on a patient 120. In the example of FIG. 1, the robotic system 110 couples to a scope 130 and an electromagnetic (EM) field generator 140. The medical system 100 also includes a control system 150 configured to interface with the robotic system 110, provide information regarding the procedure, and/or perform a variety of other operations. For example, the control system 150 can include a display(s) 152 configured to present certain information to assist a physician 160 in performing the procedure. The medical system 100 can include a table 170 (e.g., bed) to hold the patient 120. Various acts are described herein as being performed by the physician 160. These acts can be performed directly by the physician 160, a user under the direction of the physician 160, another user (e.g., a technician), a combination thereof, and/or any other user. The devices/components of the medical system 100 can be arranged in a variety of ways depending on the type procedure and/or phase of the procedure.

The control system 150 can operate in cooperation with the robotic system 110 to perform a medical procedure on the patient 120. For example, the control system 150 can communicate with the robotic system 110 via a wireless or wired connection to control a medical instrument connected to the robotic system 110, receive an image(s) captured by a medical instrument, and so on. For example, the control system 150 can receive image data from the scope 130 (e.g., an imaging device associated with the scope 130) and display the image data (and/or representations generated therefrom) to the physician 160 to assist the physician 160 in navigating the scope 130 within the patient 120. The physician 160 can provide input via an input/output (I/O) device, such as a controller 154, and the control system 150 can send control signals to the robotic system 110 to control movement of the scope 130 connected to the robotic system 110. The scope 130 (and/or another medical instrument) can be configured to move in a variety of manners, such as to articulate within a plane(s), roll, and so on, as discussed in further detail below.

In some embodiments, the control system 150 can provide fluids to the robotic system 110 via one or more fluid channels, provide power to the robotic system 110 via one or more electrical connections, provide optics to the robotic system 110 via one or more optical fibers or other components, and so on. In examples, the control system 150 can communicate with a medical instrument to receive sensor data (via the robotic system 110 and/or directly from the medical instrument). Sensor data can indicate or be used to determine a position and/or orientation of the medical instrument. Further, in examples, the control system 150 can communicate with the table 170 to position the table 170 in a particular orientation or otherwise control the table 170. Moreover, in examples, the control system 150 can communicate with the EM field generator 140 to control generation of an EM field around the patient 120.

The robotic system 110 can include one or more robotic arms 112 configured to engage with and/or control a medical instrument(s)/device. Each robotic arm 112 can include multiple arm segments coupled to joints, which can provide multiple degrees of movement. A distal end of a robotic arm 112 (e.g., end effector) can be configured to couple to an instrument/device. In the example of FIG. 1, the robotic arm 112(A) is coupled to the EM field generator 140, which can be configured to generate an EM field that is detected by a sensor on a medical instrument, such as an EM sensor on the scope 130. The second robotic arm 112(B) is coupled to a scope-driver instrument coupling 132, which can facilitate robotic control/advancement of the scope 130. Further, the third robotic arm 112(C) is coupled to a handle 134 of the scope 130, which can be configured to facilitate advancement and/or operation of a medical instrument that can be deployed through the scope 130, such as an instrument deployed through a working channel of the scope 130. In this example, the second robotic arm 112(B) and/or the third robotic arm 112(C) can control movement of the scope 130 (e.g., articulation, roll, etc.). Although three robotic arms are connected to particular medical instruments in FIG. 1, the robotic system 110 can include any number of robotic arms that are configured to connect to any type of medical instrument/device.

The robotic system 110 can be communicatively coupled to any component of the medical system 100. For example, the robotic system 110 can be communicatively coupled to the control system 150 to receive a control signal from the control system 150 to perform an operation, such as to control a robotic arm 112 in a particular manner, manipulate a medical instrument, and so on. Further, the robotic system 110 can be configured to receive an image (also referred to as image data) from the scope 130 depicting internal anatomy of the patient 120 and/or send the image to the control system 150, which can then be displayed on the display(s) 152. Moreover, the robotic system 110 can be coupled to a component of the medical system 100, such as the control system 150, in a manner as to allow for fluids, optics, power, or the like to be received therefrom.

A medical instrument can include a variety of types of instruments, such as a scope (sometimes referred to as an "endoscope"), a catheter, a needle, a guidewire, a lithotripter, a basket retrieval device, forceps, a vacuum, a needle, a scalpel, an imaging probe, an imaging device, jaws, scissors, graspers, needle holder, micro dissector, staple applier, tacker, suction/irrigation tool, clip applier, and so on. A medical instrument can include a direct entry instrument, percutaneous entry instrument, and/or another type of instrument. In some embodiments, a medical instrument is a steerable device, while in other embodiments a medical instrument is a non-steerable device. In some embodiments, a surgical tool refers to a device that is configured to puncture or to be inserted through the human anatomy, such as a needle, a scalpel, a guidewire, and so on. However, a surgical tool can refer to other types of medical instruments.

The term "scope" or "endoscope" can refer to any type of elongate medical instrument having image generating, viewing, and/or capturing functionality (or configured to provide such functionality with an imaging device deployed though a working channel) and configured to be introduced into any type of organ, cavity, lumen, chamber, and/or space of a body. For example, a scope or endoscope, such as the scope 130, can refer to a ureteroscope (e.g., for accessing the urinary tract), a laparoscope, a nephroscope (e.g., for accessing the kidneys), a bronchoscope (e.g., for accessing an airway, such as the bronchus), a colonoscope (e.g., for accessing the colon), an arthroscope (e.g., for accessing a joint), a cystoscope (e.g., for accessing the bladder), a borescope, and so on. A scope/endoscope, in some instances, may comprise a rigid or flexible tube and/or may be dimensioned to be passed within an outer sheath, catheter, introducer, or other lumen-type device, or may be used without such devices. In some embodiments, a scope includes one or more working channels through which additional tools/ medical instruments, such as lithotripters, basketing devices, forceps, laser devices, imaging devices, etc., can be introduced into a treatment site. In some cases, a working channel is offset from an imaging device and/or a longitudinal axis of the scope. Further, in some cases, a scope can be configured to move based on different articulation planes, such that the scope moves with more/less freedom in a particular direction when oriented in a particular manner. For example, a scope can be associated with a primary articulation plane and a secondary articulation plane, wherein a tip of the scope is configured to move with a greater degree of freedom (e.g., with more deflection, larger bend radius, etc.) in the primary articulation plane in comparison to the secondary articulation plane. The primary articulation plane can be perpendicular to the secondary articulation plane, for example.

The terms "direct entry" or "direct access" can refer to any entry of instrumentation through a natural or artificial opening in a patient's body. For example, the scope 130 may be referred to as a direct access instrument, since the scope 130 enters into the urinary tract of a patient via the urethra.

The terms "percutaneous entry" or "percutaneous access" can refer to entry, such as by puncture and/or minor incision, of instrumentation through the skin of a patient and any other body layers necessary to reach a target anatomical location associated with a procedure (e.g., the calyx network of the kidney). As such, a percutaneous access instrument may refer to a medical instrument, device, or assembly that is configured to puncture or to be inserted through skin and/or other tissue/anatomy, such as a needle, scalpel, guidewire, sheath, shaft, scope, catheter, and the like. However, it should be understood that a percutaneous access instrument can refer to other types of medical instruments in the context of the present disclosure. In some embodiments, a percutaneous access instrument refers to an instrument/ device that is inserted or implemented with a device that facilitates a puncture and/or minor incision through the skin of a patient. For example, a catheter may be referred to as a percutaneous access instrument when the catheter is inserted through a sheath/shaft that has punctured the skin of a patient.

In some embodiments, a medical instrument includes a sensor (also referred to as a "position sensor") that is configured to generate sensor data. In examples, sensor data can indicate a position and/or orientation of the medical instrument and/or can be used to determine a position and/or orientation of the medical instrument. For instance, sensor data can indicate a position and/or orientation of a scope, which can indicate a roll of a distal end of the scope. A position and orientation of a medical instrument can be referred to as a pose of the medical instrument. A sensor can be positioned on a distal end of a medical instrument and/or any other location. In some embodiments, a sensor can provide sensor data to the control system 150, the robotic system 110, and/or another system/device to perform one or more localization techniques to determine/track a position and/or an orientation of a medical instrument.

In some embodiments, a sensor can include an electromagnetic (EM) sensor with a coil of conductive material. Here, an EM field generator, such as the EM field generator 140, can provide an EM field that is detected by the EM sensor on the medical instrument. The magnetic field can induce small currents in coils of the EM sensor, which can be analyzed to determine a distance and/or angle/orientation between the EM sensor and the EM field generator. Further, a sensor can include another type of sensor, such as a camera, a range sensor (e.g., depth sensor), a radar device, a shape sensing fiber, an accelerometer, a gyroscope, an accelerometer, a satellite-based positioning sensor (e.g., a global positioning system (GPS)), a radio-frequency transceiver, and so on.

In some embodiments, the medical system 100 can also include an imaging device (not illustrated in FIG. 1) which can be integrated into a C-arm and/or configured to provide imaging during a procedure, such as for a fluoroscopy-type procedure. The imaging device can be configured to capture/ generate one or more images of the patient 120 during a procedure, such as one or more x-ray or CT images. In examples, images from the imaging device can be provided in real-time to view anatomy and/or medical instruments within the patient 120 to assist the physician 160 in performing a procedure. The imaging device can be used to perform a fluoroscopy (e.g., with a contrast dye within the patient 120) or another type of imaging technique.

The various components of the medical system 100 can be communicatively coupled to each other over a network, which can include a wireless and/or wired network. Example networks include one or more personal area networks (PANs), local area networks (LANs), wide area networks (WANs), Internet area networks (IANs), cellular networks, the Internet, etc. Further, in some embodiments, the components of the medical system 100 are connected for data communication, fluid/gas exchange, power exchange, and so on, via one or more support cables, tubes, or the like.

In some embodiments, the medical system 100 can provide information to assist the physician 160 in controlling the scope 130 and/or a tool deployed through the scope 130. For example, the control system 150 can display an image representation 154 in an interface 156, wherein the image representation 154 includes or is based on image data captured by an imaging device associated with the scope 130. The imaging device can be disposed on a distal end of the scope 130, deployed out the distal end of the scope 130 through a working channel of the scope 130, or otherwise associated with the scope 130. In the example of FIG. 1, the image representation 154 depicts an internal view of the kidney 190 of the patient 120 (i.e., from the perspective of the scope 130 within a calyx 191 of the kidney 190). Further, the control system 150 can provide a working channel indicator 158 that indicates an angle of rotation of a working channel of the scope 130 relative to the image representation 154. For example, the location of the working channel indicator 158(A) within the interface 156(A) indicates that the working channel is located on the right side in FIG. 1 with respect to the image representation 154(A). Although not illustrated in FIG. 1, the control system 150 can also provide other types of indicators, such as an indicator for an orientation of an articulation plane of the scope 130, an indicator for an orientation of a light associated with the scope 130, an indicator for a position/orientation of a needle/catheter/other instrument that is rendezvousing with the scope 130, and so on.

In some embodiments, the control system 150 can adjust the image representation 154 and/or the working channel indicator 158 to reflect a change in orientation of the scope 130. For example, the control system 150 can rotate the working channel indicator 158 when the scope 130 rolls to accurately indicate the orientation of the working channel relative to the image representation 154. Further, the control system 150 can adjust the orientation of the image representation 154 to provide a same virtual horizon/frame of reference before and after a roll. For example, the control system 150 can rotate the image representation 154 when the scope 130 rolls so that the view of the internal anatomy of the patient 120 has the same orientation before and after the scope 130 rolls.

To illustrate, assume that the scope 130 is positioned in the kidney 190 in proximity to a kidney stone 192 and includes a laser device deployed through a working channel to break up the kidney stone 192, as illustrated in FIG. 1. Also, assume that the scope 130 is initially positioned with a first orientation that can cause a laser from the laser device to miss the kidney stone 192 (i.e., extend along a path 193 that contacts that anatomy of the patient 120). Here, the control system 150 can display the interface 156(A) with the working channel indicator 158(A) positioned on the right. To adjust the orientation of the laser device, the physician 160 can cause the scope 130 to roll to a second orientation in which a laser from the laser device can contact the kidney stone 192 (i.e., extend along a path 194). In this illustration, the scope 130 is rolled 180 degrees. However, the scope 130 can be rolled any number of degrees. The control system 150 can then present the updated user interface 156(B) that includes the updated working channel indicator 158(B). The control system 150 can also rotate the image data 156 180 degrees to present the same horizon within the image data 156, as shown in the updated user interface 156(B). That is, the control system 150 can adjust the orientation of the image data 156 within the user interface 156 so that the frame of reference within the patient 120 is maintained (e.g., the kidney stone 192 appears on the left both before and after rolling the scope 130). By adjusting the image representation 154 and/or the working channel indicator 158 in such a manner a frame of reference within the patient 120 can be maintained. In other solutions, such roll of the scope 130 would cause the image representation 154 to rotate 180 degrees from the initial orientation, which can cause the physician 160 to become disoriented.

In some embodiments, the control system 150 can apply an orientation adjustment to the image representation 154 (and/or the working channel indicator 158) after the scope 130 has completed a roll. For example, in response to determining that the scope 130 has rolled 180 degrees, the control system 150 can rotate the image representation 154 to the view illustrated in the user interface 156(B). Here, the physician 160 can perceive the content in the image representation 154 as rotating 180 degrees and then rotating back 180 degrees following the roll of the scope 130. An example of such orientation adjustment is discussed below in reference to FIGS. 4-1 through 4-9. Alternatively, in some embodiments, the control system 150 can continuously update the user interface 156 to maintain a frame of reference within the patient 120. For example, the control system 150 can track a roll of the scope 130 and continuously update the image representation 154 to maintain a virtual horizon within the patient 120 throughout the roll of the scope 130. Here, the physician 160 can perceive the image representation 154 as remaining the same, while the working channel indicator 158 rotates around the image representation 154. An example of such continuous orientation adjustment is discussed below in reference to FIGS. 5-1 through 5-5.

In some examples, the medical system 100 is implemented to perform a medical procedure relating to the renal anatomy, such as to treat kidney stones. Kidney stone disease, also known as urolithiasis, is a medical condition that involves the formation in the urinary tract of a solid piece of material, referred to as "kidney stones," "urinary stones," "renal calculi," "renal lithiasis," or "nephrolithiasis." Urinary stones may be formed and/or found in the kidneys, the ureters, and the bladder (referred to as "bladder stones"). Such urinary stones can form as a result of mineral concentration in urinary fluid and can cause significant abdominal pain once such stones reach a size sufficient to impede urine flow through the ureter or urethra. Urinary stones may be formed from calcium, magnesium, ammonia, uric acid, cysteine, and/or other compounds or combinations thereof.

Generally, there are several methods for treating patients with kidney stones, including observation, medical treatments (such as expulsion therapy), non-invasive treatments (such as extracorporeal shock wave lithotripsy (ESWL)), and surgical treatments (such as ureteroscopy and percutaneous nephrolithotomy ("PCNL")). In surgical approaches (e.g., ureteroscopy and PCNL), the physician gains access to the pathology (i.e., the object to be removed; e.g., the stone), the stone is broken into smaller pieces or fragments, and the relatively small stone fragments/particulates are mechanically extracted from the kidney.

To remove urinary stones from the bladder and ureter, physicians may insert a ureteroscope into the urinary tract through the urethra. Typically, a ureteroscope includes an endoscope at its distal end configured to enable visualization of the urinary tract. The ureteroscope can also include a lithotripsy device to capture or break apart urinary stones. During the procedure, one physician/technician may control the position of the ureteroscope, while another other physician/technician may control the lithotripsy device(s). In order to remove relatively large stones from the kidneys (i.e., "kidney stones"), physicians may use a percutaneous nephrolithotomy ("PCNL") technique that involves inserting a nephroscope through the skin (i.e., percutaneously) and intervening tissue to provide access to the treatment site for breaking-up and/or removing the stone(s).

In several of the examples described herein, robotic-assisted percutaneous procedures can be implemented in connection with various medical procedures, such as kidney stone removal procedures, wherein robotic tools (e.g., one or more components of the medical system 100) can enable a physician/urologist to perform endoscopic (e.g., ureteroscopy) target access as well as percutaneous access/treatment. This disclosure, however, is not limited to kidney stone removal and/or robotic-assisted procedures. In some implementations, robotic medical solutions can provide relatively higher precision, superior control, and/or superior hand-eye coordination with respect to certain instruments compared to strictly manual procedures. For example, robotic-assisted percutaneous access to the kidney in accordance with some procedures can advantageously enable a urologist to perform both direct-entry endoscopic renal access and percutaneous renal access. Although some embodiments of the present disclosure are presented in the context of catheters, nephroscopes, ureteroscopes, and/or the human renal anatomy, it should be understood that the principles disclosed herein may be implemented in any type of endoscopic/percutaneous procedure or another type of procedure.

In one illustrative and non-limiting procedure, the medical system 100 can be used to remove a kidney stone 192 from the patient 120. During setup for the procedure, the physician 160 can position the robotic arms 112 of the robotic system 110 in the desired configuration and/or attach the appropriate medical instruments. For example, as shown in FIG. 1, the physician 160 can position the first robotic arm 112(A) near a treatment site and attach the EM field generator 140, which can assist in tracking a location of the scope 130 and/or other instruments/devices during the procedure. Further, the physician 160 can position the second robotic arm 112(B) between the legs of the patient 120 and attach the scope-driver instrument coupling 132, which can facilitate robotic control/advancement of the scope 130. The physician 160 can insert a medical instrument 136 into the urethra 195 of the patient 120, through the bladder 196, and/or up the ureter 197. The physician 160 can connect the medical instrument 136 to the scope-drive instrument coupling 132. The medical instrument 136 can include a lumen-type device configured to receive the scope 130 (e.g., an access sheath), thereby assisting in inserting the scope 130 into the anatomy of the patient 120. Although the medical instrument 136 is illustrated in FIG. 1, in some embodiments the medical instrument 136 is not used (e.g., the scope 130 is inserted directly into the urethra 195). The physician 160 can then insert the scope 130 into the medical instrument 136 manually, robotically, or a combination thereof. The physician 160 can attach the handle 134 of the scope 130 to the third robotic arm 112(C), which can be configured to facilitate advancement and/or operation of a basketing device, laser device, and/or another medical instrument deployed through the scope 130.

The physician 160 can interact with the control system 150 to cause the robotic system 110 to advance and/or navigate the scope 130 into the kidney 190. For example, the physician 160 can navigate the scope 130 to locate the kidney stone 192. The control system 150 can provide information via the display(s) 152 regarding the scope 130 to assist the physician 160 in navigating the scope 130, such as the interface 156 to view the image representation 154 (e.g., a real-time image(s) captured by the scope 130), the working channel indicator 158 (e.g., indicating a current orientation of the working channel), and so on. In some embodiments, the control system 150 can use localization techniques to determine a position and/or an orientation of the scope 130, which can be viewed by the physician 160 through the display(s) 152. Further, other types of information can also be presented through the display(s) 152 to assist the physician 160 in controlling the scope 130, such as x-ray images of the internal anatomy of the patient 120.

Once at the site of the kidney stone 192 (e.g., within the calyx 191 of the kidney 190), the scope 130 can be used to designate/tag a target location for a catheter to access the kidney 190 percutaneously. To minimize damage to the kidney 190 and/or the surrounding anatomy, the physician 160 can designate a papilla as the target location for entering into the kidney 190 percutaneously. However, other target locations can be designated or determined. In some embodiments of designating the papilla, the physician 160 can navigate the scope 130 to contact the papilla, the control system 150 can use localization techniques to determine a location of the scope 130 (e.g., a location of the distal end of the scope 130), and the control system 150 can associate the location of the scope 130 with the target location. Further, in some embodiments, the physician 160 can navigate the scope 130 to be within a particular distance to the papilla (e.g., park in front of the papilla) and provide input indicating that the target location is within a field-of-view of the scope 130. The control system 150 can perform image analysis and/or other localization techniques to determine a location of the target location. Moreover, in some embodiments, the scope 130 can deliver a fiducial to mark the papilla as the target location.

When the target location is designated, a catheter (not illustrated) can be inserted through a percutaneous access path into the patient 120 to reach the target site. For example, the catheter can be connected to the first robotic arm 112(A) (upon removing the EM field generator 140) and the physician 160 can interact with the control system 150 to cause the robotic system 110 to advance and/or navigate the catheter. In some embodiments, a needle or another medical instrument is inserted into the patient 120 to create the percutaneous access path. The control system 150 can provide information via the display(s) 152 regarding the catheter to assist the physician 160 in navigating the catheter. For example, an interface(s) can provide image data from the perspective of the scope 130. The image data may depict the catheter (e.g., when within the field-of-view of an imaging device of the scope 130).

With the scope 130 and/or the catheter located at the target location, the physician 160 can use the scope 130 to break up the kidney stone 192 and/or use the catheter to extract pieces of the kidney stone 192 from the patient 120. For example, the scope 130 can deploy a tool (e.g., a laser, a cutting instrument, etc.) through a working channel to fragment the kidney stone 192 into pieces and the catheter can suck out the pieces from the kidney 190 through the percutaneous access path. In examples, the catheter and/or the scope 130 can provide irrigation and/or aspiration to facilitate removal of the kidney stone 192. For instance, the catheter (and/or associated medical instrument) can be coupled to an irrigation and/or aspiration system.

At any point before, during, or after the procedure, the physician 160 can cause the scope 130 to roll to provide a more optimal position/orientation of the scope 130. In one example, when positioning the scope 130 to break up/extract the kidney stone 192, the physician 160 can cause the scope 130 to roll to reposition a working channel of the scope 130, thereby providing a more optimal orientation to deploy an instrument through the working channel. In another example, the scope 130 can be associated with different articulation planes (e.g., primary and secondary planes). Here, the physician 160 can control the scope 130 to roll to reposition an articulation plane, so that the scope 130 can articulate in a more optimal manner (e.g., bend with more deflection). In some instances, the physician 160 can provide input to rotate the scope 130 by a predetermined amount, such as to flip the working channel 180 degrees. In other instances, the physician 160 can provide input to rotate the scope 130 by any number of degrees. In any case, when the scope 130 rolls, the control system 150 can update the working channel indicator 158 in the user interface 156 to maintain an accurate orientation of the working channel indicator 158 relative to the image representation 154. Further, the control system 150 can apply an orientation adjustment to the image representation 154 to maintain a frame of reference of the image representation 154. This can allow the physician 160 to stay oriented within the kidney 190 of the patient 120 and view an accurate orientation of the working channel relative to the image representation 154/user interface.

In some embodiments, the control system 150 and/or the robotic system 110 prevent the scope 130 from rolling (and thus, the working channel from rolling) when the scope 130 is articulated more than a particular number of degrees from a longitudinal axis (e.g., 20 degrees, 30 degrees, etc.). For example, when user input is received to flip a working channel of the scope 130, the control system 150 and/or the robotic system 110 can prevent a working channel flip if the scope 130 is articulated more than 30 degrees. However, the scope 130 can be rolled when articulated by any amount in some cases.

Although many examples are discussed in the context of displaying data associated with a scope (e.g., displaying image data associated with the scope, displaying a working channel indicator associated with the scope, etc.), the techniques can be implemented in the context of other medical instruments. For example, the techniques can be implemented to present information associated with another type of medical instrument that includes/deploys an imaging device.

Furthermore, although many examples present an indicator for a working channel, other types of indicators can be presented. For example, the techniques can display an articulation plane indicator indicating an orientation of an articulation plane of a medical instrument relative to an image representation within a user interface, a light indicator for a light disposed on a distal end of the medical instrument (which can indicate an orientation of the light relative to an image representation), a needle/catheter/instrument indicator for a needle/catheter/other instrument that is rendezvousing with the medical instrument (which can indicate an orientation of the needle/catheter/instrument relative to an image representation), and so on. Such indicators can be oriented/updated within a user interface as a scope/medical instrument rolls to accurately indicate an orientation of the item that the indicator represents. In some instances, a needle/catheter/instrument that is rendezvousing with a scope can be out of the field of view of the scope, and thus, the needle/catheter/instrument is not displayed in an image representation from the perspective of the scope (e.g., the needle/catheter/instrument is off screen). Here, a needle/catheter/instrument indicator can still be maintained in the appropriate orientation within the image representation before and after rolling the scope. For example, a needle/catheter/instrument indicator can be positioned on the right in a user interface (indicating that the needle/catheter/instrument is off screen to the right). Such positioning of the needle/catheter/instrument indicator can be the same both before and after rolling the scope, assuming that the needle/catheter/instrument is not moved. In examples, position/orientation information about the needle/catheter/instrument can be obtained based on a position sensor in the needle/catheter/instrument, such as an EM sensor or shape sensing.

In many examples, a roll of the scope 130 is controlled by the robotic arm 112 while the robotic arm 112 remains in a relatively stationary position (e.g., the end effector of the robotic arm 112 can stay in the same position). For example, the robotic arm 112 can control/drive a roll feature/mechanism on the scope 130 to cause the scope 130 to roll. However, the scope 130 can roll by rolling the end effector of the robotic arm 112 in some cases. For example, the end effector can roll relative to a longitudinal axis of the scope 130, such that the handle 134 of the scope 130 rolls around the longitudinal axis.

The medical system 100 can provide a variety of benefits, such as providing guidance to assist a physician in performing a procedure (e.g., instrument tracking, instrument navigation, instrument calibration, etc.), enabling a physician to perform a procedure from an ergonomic position without the need for awkward arm motions and/or positions, enabling a single physician to perform a procedure with one or more medical instruments, avoiding radiation exposure (e.g., associated with fluoroscopy techniques), enabling a procedure to be performed in a single-operative setting, providing continuous suction to remove an object more efficiently (e.g., to remove a kidney stone), and so on. For example, the medical system 100 can provide guidance information to assist a physician in using various medical instruments to access a target anatomical feature while minimizing bleeding and/or damage to anatomy (e.g., critical organs, blood vessels, etc.). Further, the medical system 100 can provide non-radiation-based navigational and/or localization techniques to reduce physician and patient exposure to radiation and/or reduce the amount of equipment in the operating room. Moreover, the medical system 100 can provide functionality that is distributed between at least the control system 150 and the robotic system 110, which can be independently movable. Such distribution of functionality and/or mobility can enable the control system 150 and/or the robotic system 110 to be placed at locations that are optimal for a particular medical procedure, which can maximize working area around the patient and/or provide an optimized location for a physician to perform a procedure.

Although various techniques/systems are discussed as being implemented as robotically-assisted procedures (e.g., procedures that at least partly use the medical system 100), the techniques/systems can be implemented in other procedures, such as in fully-robotic medical procedures, human-only procedures (e.g., free of robotic systems), and so on. For example, the medical system 100 can be used to perform a procedure without a physician holding/manipulating a medical instrument and without a physician controlling movement of a robotic system/arm (e.g., a fully-robotic procedure that relies on relatively little input to direct the procedure). That is, medical instruments that are used during a procedure can each be held/controlled by components of the medical system 100, such as the robotic arms 112 of the robotic system 110.

Example Control System and Robotic System

Figures 1, 2, 3, 4:
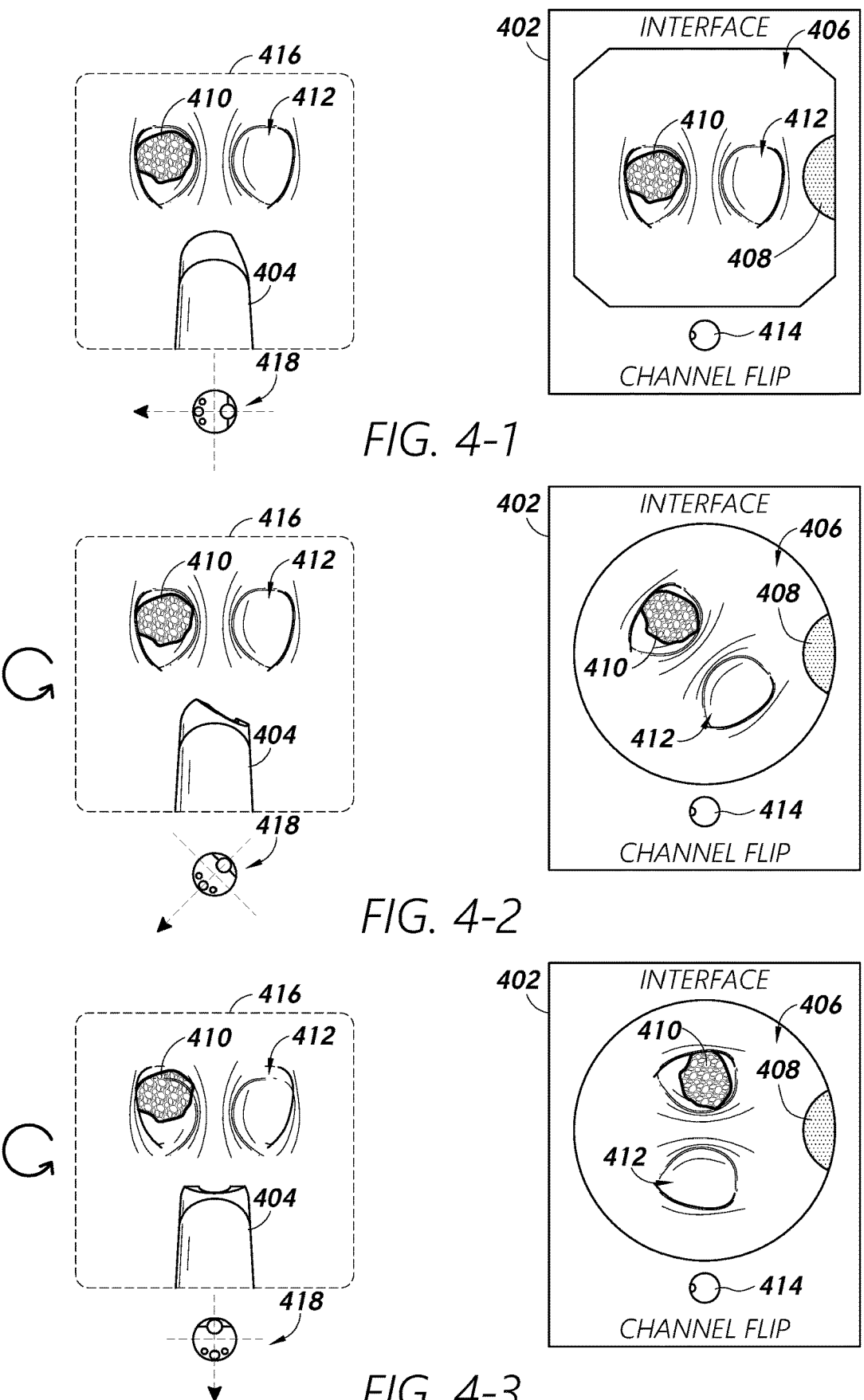

FIG. 2 shows example details of the control system 150 and the robotic system 110 of FIG. 1 in accordance with one or more embodiments. Although certain components of the control system 150 and/or the robotic system 110 are illustrated in FIG. 2, it should be understood that additional components not shown can be included in embodiments in accordance with the present disclosure. Furthermore, any of the illustrated components can be omitted, interchanged, and/or integrated into other devices/systems, such as the table 170, a medical instrument, etc.

With reference to FIG. 2, the control system 150 can include one or more of the following components, devices, modules, and/or units (referred to herein as "components"), either separately/individually and/or in combination/collectively: one or more I/O components 202, one or more communication interfaces 204, one or more power supply units 206, and/or one or more mobilization components 208 (e.g., casters or other types of wheels). In some embodiments, the control system 150 can comprise a housing/enclosure configured and/or dimensioned to house or contain at least part of one or more of the components of the control system 150. In this example, the control system 150 is illustrated as a cart-based system that is movable with the one or more mobilization components 208. In some cases, after reaching the appropriate position, the one or more mobilization components 208 can be immobilized using wheel locks to hold the control system 150 in place. However, the control system 150 can be implemented as a stationary system, integrated into another system/device, and so on.

The various components of the control system 150 can be electrically and/or communicatively coupled using certain connectivity circuitry/devices/features, which may or may not be part of control circuitry. For example, the connectivity feature(s) can include one or more printed circuit boards configured to facilitate mounting and/or interconnectivity of at least some of the various components/circuitry of the control system 150. In some embodiments, two or more of the components of the control system 150 can be electrically and/or communicatively coupled to each other.

The one or more I/O components/devices 202 can include a variety of components to receive input and/or provide output, such as to interface with a user to assist in performing a medical procedure. The one or more I/O components 202 can be configured to receive touch, speech, gesture, or any other type of input. In examples, the one or more I/O components 202 can be used to provide input regarding control of a device/system, such as to control the robotic system 110, navigate a scope or other medical instrument attached to the robotic system 110 and/or deployed through the scope, control the table 170, control a fluoroscopy device, and so on. For example, the physician 160 (not illustrated) can provide input via the I/O component(s) 202 and, in response, the control system 150 can send control signals to the robotic system 110 to manipulate a medical instrument. In examples, the physician 160 can use the same I/O device to control multiple medical instruments (e.g., switch control between the instruments).

As shown, the one or more I/O components 202 can include the one or more displays 152 (sometimes referred to as "the one or more display devices 152") configured to display data. The one or more displays 152 can include one or more liquid-crystal displays (LCD), light-emitting diode (LED) displays, organic LED displays, plasma displays, electronic paper displays, and/or any other type(s) of technology. In some embodiments, the one or more displays 152 include one or more touchscreens configured to receive input and/or display data. Further, the one or more I/O components 202 can include one or more I/O devices/controls 210, which can include a touch pad, controller (e.g., hand-held controller, video-game-type controller, tactile interface, haptic interface, finger-based controls/finger clutch(es) that enable finger-like movement, etc.), mouse, keyboard, wearable device (e.g., optical head-mounted display), virtual or augmented reality device (e.g., head-mounted display), foot panel (e.g., buttons at the user's feet), etc. Additionally, the one or more I/O components 202 can include one or more speakers configured to output sounds based on audio signals and/or one or more microphones configured to receive sounds and generate audio signals. In some embodiments, the one or more I/O components 202 include or are implemented as a console.

In some embodiments, the one or more I/O components 202 can output information related to a procedure. For example, the control system 150 can receive real-time images that are captured by a scope and display the real-time images and/or visual/image representations of the real-time images via the display(s) 152. The display(s) 152 can present an interface(s), such as any of the interfaces discussed herein, which can include image data from the scope and/or another medical instrument. Additionally, or alternatively, the control system 150 can receive signals (e.g., analog, digital, electrical, acoustic/sonic, pneumatic, tactile, hydraulic, etc.) from a medical monitor and/or a sensor associated with a patient, and the display(s) 152 can present information regarding the health or environment of the patient. Such information can include information that is displayed via a medical monitor including, for example, a heart rate e.g., ECG, HRV, etc.), blood pressure/rate, muscle bio-signals (e.g., EMG), body temperature, blood oxygen saturation (e.g., $SpO_2$), $CO_2$, brainwaves (e.g., EEG), environmental and/or local or core body temperature, and so on.

The one or more communication interfaces 204 can be configured to communicate with one or more devices/sensors/systems. For example, the one or more communication interfaces 204 can send/receive data in a wireless and/or wired manner over a network. A network in accordance with embodiments of the present disclosure can include a local area network (LAN), wide area network (WAN) (e.g., the Internet), personal area network (PAN), body area network (BAN), etc. In some embodiments, the one or more communication interfaces 204 can implement a wireless technology, such as Bluetooth, Wi-Fi, near field communication (NFC), or the like.

The one or more power supply units 206 can be configured to manage and/or provide power for the control system 150 (and/or the robotic system 110, in some cases). In some embodiments, the one or more power supply units 206 include one or more batteries, such as a lithium-based battery, a lead-acid battery, an alkaline battery, and/or another type of battery. That is, the one or more power supply units 206 can comprise one or more devices and/or circuitry configured to provide a source of power and/or provide power management functionality. Moreover, in some embodiments the one or more power supply units 206 include a mains power connector that is configured to couple to an alternating current (AC) or direct current (DC) mains power source.

Although not shown in FIG. 2, the control system 150 can include and/or control other components, such as one or more pumps, flow meters, valve controls, and/or fluid access components in order to provide controlled irrigation and/or aspiration capabilities to a medical instrument, a device that can be deployed through a medical instrument, and so on. In some embodiments, irrigation and aspiration capabilities can be delivered directly to a medical instrument through a separate cable(s). Further, the control system 150 can include a voltage and/or surge protector designed to provide filtered and/or protected electrical power to another device, such as the robotic system 110, thereby avoiding placement of a power transformer and/or other auxiliary power components in robotic system 110, resulting in a smaller, more moveable robotic system 110.

In some embodiments, the control system 150 can include support equipment for sensors deployed throughout the medical system 100. For example, the control system 150 can include opto-electronics equipment for detecting, receiving, and/or processing data received from optical sensors and/or cameras. Such opto-electronics equipment can be used to generate real-time images for display in any number of devices/systems, including in the control system 150. Similarly, the control system 150 can include an electronic subsystem for receiving and/or processing signals received from deployed electromagnetic (EM) sensors. In some embodiments, the control system 150 can also be used to house and/or position an EM field generator for detection by EM sensors in or on a medical instrument.

Further, in some embodiments, the control system 150 can be coupled to the robotic system 110, the table 170, and/or a medical instrument, through one or more cables or connections (not shown). In some implementations, support functionality from the control system 150 can be provided through a single cable, simplifying and de-cluttering an operating room. In other implementations, specific functionality can be coupled in separate cabling and connections. For example, while power can be provided through a single power cable, the support for controls, optics, fluidics, and/or navigation can be provided through a separate cable.

The robotic system 110 generally includes an elongate support structure 210 (also referred to as a "column"), a robotic system base 212, and a console 214 at the top of the column 210. The column 210 can include one or more carriages 216 (also referred to as "the arm support 216") for supporting the deployment of one or more the robotic arms 112. The carriage 216 can include individually configurable arm mounts that rotate along a perpendicular axis to adjust the base of the robotic arms 112 for positioning relative to a patient. The carriage 216 also includes a carriage interface 218 that allows the carriage 216 to vertically translate along the column 210. The carriage interface 218 can be connected to the column 210 through slots, such as slot 220, that are positioned on opposite sides of the column 210 to guide the vertical translation of the carriage 216. The slot 220 can include a vertical translation interface to position and/or hold the carriage 216 at various vertical heights relative to the base 212. Vertical translation of the carriage 216 allows the robotic system 110 to adjust the reach of the robotic arms 112 to meet a variety of table heights, patient sizes, physician preferences. etc. Similarly, the individually configurable arm mounts on the carriage 216 allow a robotic arm base 222 of the robotic arms 112 to be angled in a variety of configurations. The column 210 can internally comprise mechanisms, such as gears and/or motors, that are designed to use a vertically aligned lead screw to translate the carriage 216 in a mechanized fashion in response to control signals generated in response to user inputs, such as inputs from an I/O device(s).

The base 212 can balance the weight of the column 210, the carriage 216, and/or robotic arms 112 over a surface, such as the floor. Accordingly, the base 212 can house heavier components, such as one or more electronics, motors, power supply, etc., as well as components that enable movement and/or immobilize the robotic system 110. For example, the base 212 can include rollable wheels 224 (also referred to as "the casters 224" or "the mobilization components 224") that allow for the robotic system 110 to move around the room for a procedure. After reaching an appropriate position, the casters 224 can be immobilized using wheel locks to hold the robotic system 110 in place during the procedure. As shown, the robotic system 110 also includes a handle 226 to assist with maneuvering and/or stabilizing the robotic system 110. In this example, the robotic system 110 is illustrated as a cart-based system that is movable. However, the robotic system 110 can be implemented as a stationary system, integrated into a table, and so on.

The robotic arms 112 can generally comprise robotic the arm bases 222 and end effectors 228, separated by a series of linkages 230 (also referred to as "arm segments 230") that are connected by a series of joints 232. Each joint 232 can comprise an independent actuator and each actuator can comprise an independently controllable motor. Each independently controllable joint 232 represents an independent degree of freedom available to the robotic arm 112. For example, each of the arms 112 can have seven joints, and thus, provide seven degrees of freedom. However, any number of joints can be implemented with any degrees of freedom. In examples, a multitude of joints can result in a multitude of degrees of freedom, allowing for "redundant" degrees of freedom. Redundant degrees of freedom allow the robotic arms 112 to position their respective end effectors 228 at a specific position, orientation, and/or trajectory in space using different linkage positions and/or joint angles. In some embodiments, the end effectors 228 can be configured to engage with and/or control a medical instrument, a device, an object, and so on. The freedom of movement of the arms 112 can allow the robotic system 110 to position and/or direct a medical instrument from a desired point in space and/or allow a physician to move the arms 112 into a clinically advantageous position away from the patient to create access, while avoiding arm collisions.

The end effector 228 of each of the robotic arms 112 can comprise an instrument device manipulator (IDM), which may be attached using a mechanism changer interface (MCI). In some embodiments, the IDM can be removed and replaced with a different type of IDM. For example, a first type of IDM can manipulate an endoscope, a second type of IDM can manipulate a catheter, a third type of IDM can hold an EM field generator, and so on. An MCI can include connectors to transfer pneumatic pressure, electrical power, electrical signals, and/or optical signals from the robotic arm 112 to the IDM. The IDMs 228 may be configured to manipulate medical instruments (e.g., surgical tools/instruments) using techniques including, for example, direct drives, harmonic drives, geared drives, belts and pulleys, magnetic drives, and the like. In some embodiments, the IDMs 228 can be attached to respective ones of the robotic arms 112, wherein the robotic arms 112 are configured to insert or retract the respective coupled medical instruments into or out of the treatment site.

In some embodiments, the robotic arms 112 can be configured to control a position, orientation, and/or tip articulation of a medical instrument (e.g., a sheath and/or a leader of a scope) attached thereto. For example, the robotic arms 112 can be configured/configurable to manipulate a scope using elongate movement members. The elongate movement members can include one or more pull wires (e.g., pull or push wires), cables, fibers, and/or flexible shafts. To illustrate, the robotic arms 112 can be configured to actuate multiple pull wires of the scope to deflect the tip of the scope. Pull wires can include any suitable or desirable materials, such as metallic and/or non-metallic materials such as stainless steel, Kevlar, tungsten, carbon fiber, and the like. In some embodiments, the scope is configured to exhibit nonlinear behavior in response to forces applied by the elongate movement members. The nonlinear behavior can be based on stiffness and compressibility of the scope, as well as variability in slack or stiffness between different elongate movement members.

As shown, the console 214 is positioned at the upper end of column 210 of the robotic system 110. The console 214 can include a display(s) 234 to provide a user interface for receiving user input and/or providing output (e.g., a dual-purpose device, such as a touchscreen), such as to provide a physician/user with pre-operative data, intra-operative data, information to configure the robotic system 110, and so on. Potential pre-operative data can include pre-operative plans, navigation and mapping data derived from pre-operative computerized tomography (CT) scans, and/or notes from pre-operative patient interviews. Intra-operative data can include optical information provided from a tool, sensor and/or coordinate information from sensors, as well as vital patient statistics, such as respiration, heart rate, and/or pulse. The console 214 can be positioned and tilted to allow a physician to access the console 214 from the side of the column 214 opposite arm support 216. From this position, the physician may view the console 214, robotic arms 112, and patient while operating the console 214 from behind the robotic system 110.

The robotic system 110 can include one or more I/O components/devices 236 to receive input and/or provide output, such as to interface with a user. The one or more I/O components 236 can be configured to receive touch, speech, gesture, or any other type of input. In examples, the one or more I/O components 236 can be used to provide input regarding control of a device/system, such as to control/configure the robotic system 110. As shown, the one or more I/O components 236 can include the one or more displays 234 configured to display data. The one or more displays 234 can include one or more liquid-crystal displays (LCD), light-emitting diode (LED) displays, organic LED displays, plasma displays, electronic paper displays, and/or any other type(s) of technology. In some embodiments, the one or more displays 234 include one or more touchscreens configured to receive input and/or display data. Further, the one or more I/O components 236 can include one or more I/O devices/controls 238, which can include a touch pad, controller, mouse, keyboard, wearable device (e.g., optical head-mounted display), virtual or augmented reality device (e.g., head-mounted display), etc. Additionally, the one or more I/O components 236 can include one or more speakers configured to output sounds based on audio signals and/or one or more microphones configured to receive sounds and generate audio signals. In some embodiments, the one or more I/O components 236 include or are implemented as the console 214. Further, the one or more I/O components 236 can include one or more buttons that can be physically pressed, such as a button on a distal end of a robotic arm 112 (which can enable/disable an admittance control mode of the robotic arm 112).

The various components of the robotic system 110 can be electrically and/or communicatively coupled using certain connectivity circuitry/devices/features, which may or may not be part of control circuitry. For example, the connectivity feature(s) can include one or more printed circuit boards configured to facilitate mounting and/or interconnectivity of at least some of the various components/circuitry of the robotic system 110. In some embodiments, two or more of the components of the robotic system 110 can be electrically and/or communicatively coupled to each other.

The one or more communication interfaces 240 can be configured to communicate with one or more device/sensors/systems. For example, the one or more communication interfaces 240 can send/receive data in a wireless and/or wired manner over a network. A network in accordance with embodiments of the present disclosure can include a local area network (LAN), wide area network (WAN) (e.g., the Internet), personal area network (PAN), body area network (BAN), etc. In some embodiments, the one or more communication interfaces 240 can implement a wireless technology such as Bluetooth, Wi-Fi, near field communication (NFC), or the like.

The one or more power supply units 242 can be configured to manage and/or provide power for the robotic system 110. In some embodiments, the one or more power supply units 242 include one or more batteries, such as a lithium-based battery, a lead-acid battery, an alkaline battery, and/or another type of battery. That is, the one or more power supply units 242 can comprise one or more devices and/or circuitry configured to provide a source of power and/or provide power management functionality. Moreover, in some embodiments the one or more power supply units 242 include a mains power connector that is configured to couple to an alternating current (AC) or direct current (DC) mains power source. Further, in some embodiments, the one or more power supply units 242 include a connector that is configured to couple to the control system 150 to receive power from the control system 150.

The robotic system 110 can also include one or more actuators/hardware 244 to facilitate movement of the robotic arms 112. Each actuator 244 can comprise a motor, which can be implemented in a joint or elsewhere within a robotic arm 112 to facilitate movement of the joint and/or a connected arm segment/linkage. Further, the robotic system 110 can include a variety of other components, such as pneumatics, optical sources, etc.

The control system 150 and/or the robotic system 110 can include control circuitry 246 and/or data storage/memory 248 configured to perform functionality described herein. For ease of discussion and illustration, the control circuitry 246 and data storage 248 are shown in blocks between the control system 150 and the robotic system 110. It should be understood that, in many embodiments, the control system 150 and the robotic system 110 can include separate instances of the control circuitry 246 and the data storage 248. That is, the control system 150 can include its own control circuitry and data storage (e.g., to implement processing on the control system 150), while the robotic system 110 can include its own control circuitry and data storage (e.g., to implement processing on the robotic system 110). In many embodiments, reference to control circuitry may refer to circuitry embodied in a robotic system, a control system, or any other component of a medical system, such as any component of the medical system 100 shown in FIG. 1.

Although the control circuitry 246 is illustrated as a separate component from other components of the control system 150/robotic system 110, any or all of the other components of the control system 150/robotic system 110 can be embodied at least in part in the control circuitry 246. For instance, the control circuitry 246 can include various devices (active and/or passive), semiconductor materials and/or areas, layers, regions, and/or portions thereof, conductors, leads, vias, connections, and/or the like, wherein one or more of the other components of the control system 150/robotic system 110 and/or portion(s) thereof can be formed and/or embodied at least in part in/by such circuitry components/devices.

As illustrated, the data storage 248 can include a user interface component 250 configured to facilitate one or more of the user interfaces. For example, the user interface component 250 can generate user interface data and/or provide the user interface data to cause a user interface to be displayed via the display(s) 152. The user interface can include an image representation from the perspective of a medical instrument (e.g., a scope), an indicator for an element associated with the medical instrument (e.g., working channel indicator, articulation plane indicator, etc.), controls or other interface elements, and/or other information. The user interface component 250 can adjust the orientation of the image representation, such as by applying a rotation adjustment to the image representation within the user interface as the medical instrument rolls/changes orientation. The user interface component 250 can maintain the orientation of the indicator relative to the image representation to indicate an accurate orientation of the element (e.g., working channel) relative to the image representation. The user interface component 250 can use orientation/position information about a medical instrument to provide the image representation and/or working channel indicator.

The data storage 248 can also include an instrument-driving component 252 configured to drive/control a medical instrument. For example, the instrument-driving component 248 can be configured to process input signals from the I/O component(s) 202, process position/orientation data indicating a position/orientation of a medical instrument, process image orientation data indicating an orientation of image data/representation within a user interface, generate control signals for controlling the robotic system 110 and/or a medical instrument/tool connected to the robotic system 110, send the control signals to the robotic system 110 to control the robotic system 110 and/or the medical instrument/tool, and so on. In some embodiments, user control of a medical instrument can be disabled during a roll of the medical instrument to prevent unintended movement of the medical instrument and/or complications in controlling mechanical components of the robotic system 110. For example, the instrument-driving component 252 can disregard user input received once a scope roll is initiated and until the scope roll is completed, so that the user is unable to further articulate the scope during the roll.

In some embodiments, the instrument-driving component 252 can control a medical instrument to move in a correlated manner to a view provided via a user interface. For example, assume that the physician 160 is driving a scope from the perspective of the scope (e.g., based on image data from the scope that is provided via a user interface) and the physician 160 provides input via the I/O component(s) 202 to move the scope in an upward direction relative to the I/O component(s) 202, such as by selecting an up control on the I/O component(s) 202. The instrument-driving component 252 can determine an orientation/position of the scope and/or an orientation of image data/representation as displayed within the user interface. The instrument-driving component 252 can use such orientation/position information to move the scope in an upward direction on the user interface. As such, the instrument-driving component 252 can configure/update controls for a medical instrument based on an orientation of image data/representation displayed within a user interface. In examples, a manner of controlling the medical instrument can be reconfigured as the medical instrument rolls.

Further, the data storage 248 can include a localization component 254 configured to determine/track an orientation/position of an object/medical instrument. For example, the localization component 254 can process input data to generate position/orientation data for a medical instrument coupled to the robotic system 110. In some cases, the position/orientation data can indicate an amount of roll of the medical instrument. Position/orientation data of an object/medical instrument can indicate a position/orientation of the object/medical instrument relative to a frame of reference. The frame of reference can be a frame of reference relative to anatomy of a patient, a known object (e.g., an EM field generator), a coordinate system/space, and so on. In some implementations, position/orientation data can indicate a position/orientation of a distal end of a medical instrument (and/or proximal end, in some cases). For example, position/orientation data for a scope can indicate a position and orientation of a distal end of the scope, including an amount of roll of the distal end of the scope. A position and orientation of an object can be referred to as a pose of the object. In examples, techniques to determine and/or track a position and/or an orientation of the medical instrument can be referred to as localization techniques.

Example input data that can be used to generate position/orientation data for an object/medical instrument can include: sensor data from a sensor associated with a medical instrument (e.g., EM field sensor data, vision/image data captured by an imaging device/depth sensor/radar device on the medical instrument, accelerometer data from an accelerometer on the medical instrument, gyroscope data from a gyroscope on the medical instrument, optical fiber-based shape sensing, satellite-based positioning data from a satellite-based sensor (a global positioning system (GPS), for example), and so on); feedback data from a robotic arm/component (also referred to as "kinematics data") (e.g., data indicating how a robotic arm/component moved/actuated); robotic command data for a robotic arm/component (e.g., a control signal sent to the robotic system 110/robotic arm 112 to control movement of the robotic arm 112/medical instrument); model data regarding anatomy of a patient (e.g., a model of an interior/exterior portion of anatomy of the patient); position data of a patient (e.g., data indicating how the patient is positioned on a table); pre-operative data; etc.

In some implementations, the localization component 254 can use electromagnetic tracking to determine a position and/or an orientation of an object. For example, the localization component 254 can use real-time EM tracking to determine a real-time location of a medical instrument in a coordinate system/space that can be registered to the patient's anatomy, which can be represented by a pre-operative model or other model. In EM tracking, an EM sensor (or tracker) including one or more sensor coils can be embedded in one or more locations and/or orientations in a medical instrument (e.g., a scope, a needle, etc.). The EM sensor can measure a variation in an EM field created by one or more static EM field generators positioned at a known location. The location information detected by the EM sensors can be stored as EM data. The localization component 254 can process the EM data to determine a position and/or orientation of an object, such as a medical instrument. An EM field generator (or transmitter) can be placed close to the patient (e.g., within a predetermined distance) to create a low intensity magnetic field that an EM sensor can detect. The magnetic field can induce small currents in the sensor coils of the EM sensor (e.g., below a threshold), which can be analyzed to determine a distance and/or angle between the EM sensor and the EM field generator. These distances and/or orientations can be intra-operatively "registered" to patient anatomy (e.g., a pre-operative model) in order to determine a geometric transformation that aligns a single location in a coordinate system with a position in the pre-operative model of the patient's anatomy. Once registered, an EM sensor (e.g., an embedded EM tracker) in one or more positions of a medical instrument (e.g., the distal tip of an endoscope, a needle, etc.) can provide real-time indications of a position and/or an orientation the medical instrument through the patient's anatomy.

Further, in some embodiments, the localization component 254 can perform vision-based techniques to determine a position and/or an orientation of an object. For example, a medical instrument can be equipped with a camera, a range sensor (sometimes referred to as "a depth sensor"), a radar device, etc., to provide sensor data in the form of vision/image data. The localization component 254 can process the vision data to facilitate vision-based location tracking of the medical instrument. For example, a pre-operative model data can be used in conjunction with vision data to enable computer vision-based tracking of a medical instrument (e.g., an endoscope). In examples, using pre-operative model data, the control system 150 can generate a library of expected endoscopic images based on the expected path of travel of a scope, with each image being linked to a location within the model. Intra-operatively, this library can be referenced by the control system 150 in order to compare real-time images and/or other vision data captured at a scope (e.g., a camera at a distal end of an endoscope) to those in the image library to assist with localization.

Moreover, other types of vision-based techniques can be performed to determine a position and/or an orientation of an object. For example, the localization component 254 can use feature tracking to determine motion of an image sensor (e.g., a camera or other sensor), and thus, a medical instrument associated with the image sensor. In some cases, the localization component 254 can identify circular geometries in pre-operative model data that correspond to anatomical lumens and track the change of those geometries to determine which anatomical lumen is selected, as well as the relative rotational and/or translational motion of the medical instrument. Use of a topological map can also enhance vision-based algorithms or techniques. Furthermore, the localization component 254 can use optical flow, another computer vision-based technique, to analyze displacement and/or translation of image pixels in a video sequence in vision data to infer camera movement. Examples of optical flow techniques can include motion detection, object segmentation calculations, luminance, motion compensated encoding, stereo disparity measurement, etc. By comparing multiple frames over multiple iterations, the localization component 254 can determine movement and a location of an image sensor (and thus an endoscope).

Furthermore, in some embodiments, the localization component 254 can use robotic command and/or kinematics data to determine a position and/or an orientation of an object. Robotic command and/or kinematics data can be indicative of a position/orientation of a robotic arm (e.g., pitch, yaw, etc.) resulting from an articulation/actuation command. For example, robotic command and/or kinematics data can indicate an amount/direction of actuation of a joint, gear, pulley, belt, or another actuating element of a robotic arm. The localization component 254 can use data indicative of a position/orientation of a robotic arm to determine a position/orientation of a medical instrument attached to the robotic arm. For instance, based on a position/orientation of a robotic arm that is attached to a catheter, a command sent to control the catheter, and/or a characteristic(s) of the catheter (e.g., a length of the catheter, capabilities of the catheter, etc.), the localization component 254 can determine/estimate a position/orientation of the catheter. Further, in examples, the localization component 254 can use robotic command data to determine how far a medical instrument has been inserted/retracted, such as within a patient, based on commands to control the medical instrument, markings on the medical instrument indicating distance, etc. In some intra-operatively embodiments, calibration measurements can be used in combination with known insertion depth information to estimate a position and/or an orientation of a medical instrument. Alternatively, or additionally, these calculations can be analyzed in combination with EM, vision, and/or topological modeling to estimate a position and/or orientation of a medical instrument.

Further, in some embodiments, the localization component 254 can use other types of data to determine a position and/or an orientation of an object. For example, the localization component 254 can analyze sensor data from a shape sensing fiber (e.g., which can provide shape data regarding a location/shape of a medical instrument), an accelerometer, a gyroscope, a satellite-based positioning sensor (e.g., a global positioning system (GPS)), a radio-frequency transceiver, and so on, embedded on a medical instrument. Such data can be indicative of a position and/or an orientation of a medical instrument.

In some embodiments, the localization component 254 can process pre-operative data to determine a position and/or an orientation of an object. The pre-operative data (some-times referred to as "mapping data") can be generated by performing computed tomography (CT) scans, such as low dose CT scans. The pre-operative CT images from the scans can be reconstructed into three-dimensional images, which are visualized (e.g., as "slices" of a cutaway view of a patient's internal anatomy). When analyzed in the aggregate, image-based models for anatomical cavities, spaces, and/or structures of the patient's anatomy, such as a patient lung network, the renal anatomy, etc., can be generated. A centerline geometry can be determined and/or approximated from the CT images to develop a two-dimensional or three-dimensional volume of the patient's anatomy, referred to as model data (also referred to as "pre-operative model data" when generated using pre-operative CT scans). Network topological models can also be derived from CT-images.

In some embodiments, the localization component 254 can use input data in combination. For example, the localization component 254 can use a probabilistic approach where a confidence weight is assigned to a position/orientation determined from multiple forms of input data. To illustrate, if EM data is not as reliable (as may be the case where there is EM interference), the EM data can be associated with a relatively low confidence value and other forms of input data can be relied on, such as vision data, robotic command and kinematics data, and so on.

Although many embodiments are discussed in the context of the user interface component 250, the instrument-driving component 252, and/or the localization component 254 being implemented as (or including) one or more instructions that are executable by the control circuitry 246, any of these components can be implemented at least in part as control circuitry.

The term "control circuitry" can refer to any collection of one or more processors, processing circuitry, processing modules/units, chips, dies (e.g., semiconductor dies including one or more active and/or passive devices and/or connectivity circuitry), microprocessors, micro-controllers, digital signal processors, microcomputers, central processing units, graphics processing units, field programmable gate arrays, application specific integrated circuits, programmable logic devices, state machines (e.g., hardware state machines), logic circuitry, analog circuitry, digital circuitry, and/or any device that manipulates signals (analog and/or digital) based on hard coding of the circuitry and/or operational instructions. Control circuitry can further comprise one or more, storage devices, which can be embodied in a single memory device, a plurality of memory devices, and/or embedded circuitry of a device. Such data storage can comprise read-only memory, random access memory, volatile memory, non-volatile memory, static memory, dynamic memory, flash memory, cache memory, data storage registers, and/or any device that stores digital information. It should be noted that in embodiments in which control circuitry comprises a hardware state machine (and/or implements a software state machine), analog circuitry, digital circuitry, and/or logic circuitry, data storage device(s)/register(s) storing any associated operational instructions can be embedded within, or external to, the circuitry comprising the state machine, analog circuitry, digital circuitry, and/or logic circuitry.

The term "memory" can refer to any suitable or desirable type of computer-readable media. For example, computer-readable media can include one or more volatile data storage devices, non-volatile data storage devices, removable data storage devices, and/or nonremovable data storage devices implemented using any technology, layout, and/or data structure(s)/protocol, including any suitable or desirable computer-readable instructions, data structures, program modules, or other types of data.

Computer-readable media that can be implemented in accordance with embodiments of the present disclosure includes, but is not limited to, phase change memory, static random-access memory (SRAM), dynamic random-access memory (DRAM), other types of random access memory (RAM), read-only memory (ROM), electrically erasable programmable read-only memory (EEPROM), flash memory or other memory technology, compact disk read-only memory (CD-ROM), digital versatile disks (DVD) or other optical storage, magnetic cassettes, magnetic tape, magnetic disk storage or other magnetic storage devices, or any other non-transitory medium that can be used to store information for access by a computing device. As used in certain contexts herein, computer-readable media may not generally include communication media, such as modulated data signals and carrier waves. As such, computer-readable media should generally be understood to refer to non-transitory media.

Example Scope

Figure 3:
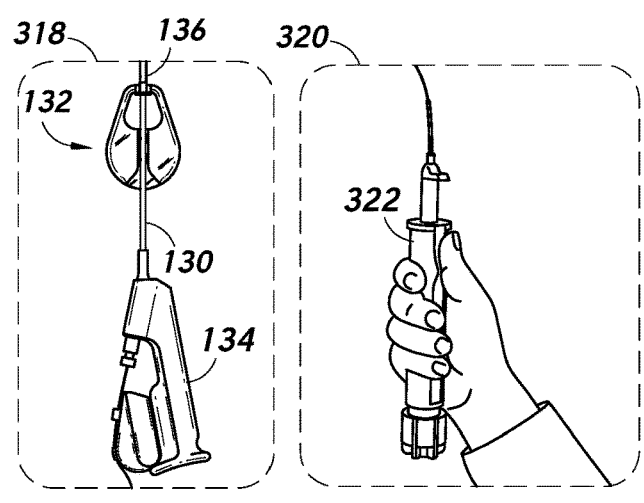
FIG. 3 illustrates an example scope disposed in portions of the urinary system of a patient in accordance with one or more embodiments.

FIG. 3 illustrates an example of the scope 130 disposed in portions of the urinary system of a patient in accordance with one or more embodiments of the present disclosure. In this example, the scope 130 is implemented as an endo-scope/ureteroscope. As referenced above, ureteroscopic procedures can be implemented for investigating abnormalities in human ureters and/or treating the same. For example, ureteroscope procedures can be implemented to treat and/or remove kidney stones. Such procedures may be implemented manually at least in part and/or may be performed using robotic technologies at least in part, such as the robotic system 110 shown in FIG. 1. For example, use of robotic devices and/or systems for certain endoscopic procedures can provide relatively greater precision, control, and/or coordination compared to strictly manual procedures.

The scope 130 can include a rigid or flexible tube, and/or can be dimensioned to be passed within an outer sheath, catheter, introducer, or other lumen-type device. However, the scope 130 can be used without such devices, in some instances. For example, the scope 130 can be configured to pass through the access sheath 136 to access the target anatomy. The access sheath 136 can have a diameter sufficient to have the scope 130 drawn therethrough, together with an object captured in by an instrument (e.g., basketing device) when the object/stone is not too large in size (e.g., within a threshold size). In some examples, the access sheath 136 may be advanced through the ureter 197 to a position near the renal pelvis 302 and/or ureteropelvic junction 304. The distal end of the access sheath 136 may be parked at a position in the ureter 197 and/or renal pelvis 302, wherein such parking position may be at least partially anatomy-dependent. However, in other examples, the access sheath 136 can be positioned within just the urethra or other anatomy without being positioned near the renal pelvis 302. Generally, the access sheath 136 may not be articulable to the degree that the scope 130 can be articulated, and therefore it may not be practical to navigate/drive the access sheath 136 into the kidney.

The scope 130 can be articulable, such as with respect to at least a distal portion of the scope, so that the scope 130 can be steered within the human anatomy. In some embodiments, the scope 130 is configured to be articulated with, for example, five degrees of freedom (DOF), including XYZ coordinate movement, as well as pitch and yaw. Further, in some embodiments, the scope 130 is articulatable with six DOF, including XYZ coordinate movement, as well as pitch, yaw, and roll. In other embodiments, the scope 130 is articulable with other DOF. In embodiments where the scope 130 is equipped with a position sensor, the position sensor can provide position information, such as 5-DOF position information (e.g., x, y, and z coordinates and pitch and yaw angles), 6-DOF position information (e.g., x, y, and z coordinate and pitch, yaw, and roll angles), and so on. In some embodiments, the scope 130 can include telescoping parts, such as an inner leader portion and an outer sheath portion, which can be manipulated to telescopically extend the scope 130.

The scope 130 can include one or more elongate movement members (not illustrated) that are configured to control movement of the scope 130, such as the distal end of the scope 130. The elongate movement members may include one or more wires (e.g., pull or push wires), cables, fibers, and/or flexible shafts. Pull wires may include any suitable or desirable materials, such as metallic and non-metallic materials such as stainless steel, Kevlar, tungsten, carbon fiber, and the like. In some embodiments, the scope 130 is configured to exhibit nonlinear behavior in response to forces applied by the elongate movement members. The nonlinear behavior may be based on stiffness and/or compressibility of the scope 130, as well as variability in slack or stiffness between different elongate movement members. For robotic implementations, a robotic arm may be configured to actuate one or more pull wires coupled to the scope 130 to deflect a tip 306 of the scope 130. In contrast, for user hand-held implementations, a user can provide manual input via an actuator to actuate one or more pull wires of the scope 130 to deflect the tip 306 of the scope 130.

The scope 130 can include an imaging device(s) 308 configured to capture image data, such as image data representing the internal anatomy of a patient. The imaging device 308 can include a camera, such as an optical camera and/or another imaging device. The imaging device 308 can include an optical fiber, fiber array, and/or lens. One or more optical components of the imaging device 308 can move along with the tip 306 of the scope 130 such that movement of the tip 306 results in changes to the images captured by the imaging device 308. In some embodiments, the scope 130 can accommodate wires and/or optical fibers to transfer signals to/from an optical assembly and the distal end 306 of the scope 130. Further, the scope 130 can be configured to accommodate optical fibers to carry light from proximately located light sources, such as light-emitting diodes, to the distal end 306 of the scope. The distal end 306 of the scope 130 can include ports for light sources 310 to illuminate an anatomical space, which may be useful when using the imaging device 308. Although multiple light sources 310 are illustrated, the scope 130 can be implemented with any number of light sources.

The scope 130 can also include a working channel 312 for deploying an instrument 314. Example instruments 314 include a laser device 314a configured to provide a laser, a basketing device 314b configured to capture/retrieve an object (e.g., a fragment of a kidney stone), forceps 314c configured to grasp/hold an object, a scalpel 314d configured to cut an object, lithotripters (not shown), an irrigation/aspiration device (not shown) configured to provide irrigation/aspiration to a target site, and so on. The working channel 312 can extend longitudinally through the scope 130 from a proximal end to the distal end 306 of the scope 130. In examples, the working channel 312 is offset to one side of the scope 130 (e.g., offset from a longitudinal axis 316 of the scope 130), such as that illustrated in FIG. 3. In other examples, the working channel 312 is positioned in the center of the scope 130 or at another location. Although the imaging device 308 is shown as being attached to the distal end 306 of the scope 130 (e.g., integral with the scope 130), in some cases the imaging device 308 is a separate device that is deployed through the working channel 312. Further, although a single working channel 312 is shown, any number of working channels may be implemented.

In some embodiments, the scope 130 includes a sensor (sometimes referred to as a "position sensor") that is configured to generate and/or send sensor data to another device. The sensor data (sometimes referred to as "sensor position data") can indicate a position and/or orientation of the scope 130 (e.g., the distal end 306 thereof) and/or can be used to determine/infer a position/orientation of the scope 130. For example, the sensor can provide sensor data to a control system, which is then used to determine a position and/or an orientation of the scope 130. The sensor can be positioned on the distal end 306 of the scope 130 and/or another location. In some embodiments, a sensor can include an electromagnetic (EM) sensor with a coil of conductive material, or another form/embodiment of an antenna. However, the scope 130 can include other types of sensors, such as a shape sensing fiber, accelerometer(s), gyroscope(s), satellite-based positioning sensor(s) (e.g., global positioning system (GPS) sensors), radio-frequency transceiver(s), and so on.

In some implementations, the scope 130 can be configured to move by different amounts in different planes, such that the scope moves with more/less freedom in a particular direction when oriented in a particular manner. For example, the scope 130 can be associated with a primary articulation plane and a secondary articulation plane, wherein the primary plane and the secondary plane are perpendicular to each other. The tip 306 of the scope 130 can be configured to move with a greater degree of freedom (e.g., exhibit more deflection) in the primary articulation plane in comparison to the secondary articulation plane.

The scope 130 and/or the instrument 314 may be controllable in any suitable or desirable way, either based on manual manipulation of a handle component(s), electronic user input, or automatically. For example, an image 318 shows an example robotic control configuration for controlling the scope 130 and/or the instrument 314 using one or more robotic arms. Here, the scope-driver instrument coupling 132 and/or the handle 134 can each be coupled to a robotic arm, which can manipulate the scope-driver instrument coupling 132 and/or the handle 134 to control the scope 130/instrument 314. Meanwhile, an image 320 shows an example manual control configuration, wherein the scope 130 includes a hand-held handle 322 that is configured to be held/manipulated by a user to facilitate movement of the scope 130/instrument 314.

Example Image/Indicator Adjustment

Figures 4, 5, 6:
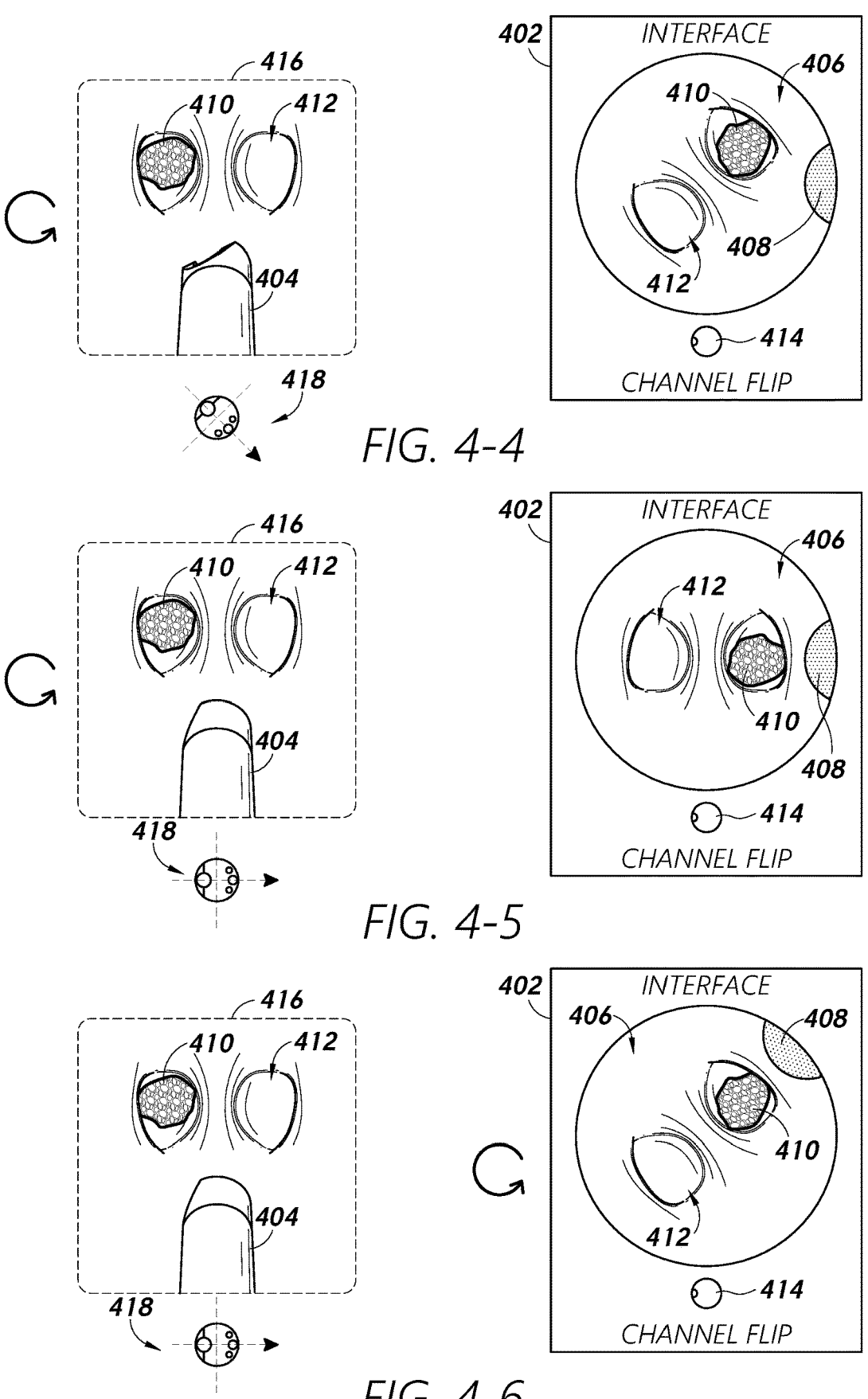

FIGS. 4-1 through 4-9 illustrate an example of rolling a scope and applying a rotation adjustment to a scope image within a user interface when the scope has completed the roll (sometimes referred to as "a phased approach") in accordance with one or more embodiments. Meanwhile, FIGS. 5-1 through 5-5 illustrate an example of rolling a scope and applying a rotation adjustment to a scope image within a user interface while the scope rolls (sometimes referred to as "a continuous approach") in accordance with one or more embodiments. In these examples, a scope rolls by a predetermined amount to cause a working channel of the scope to rotate by the same amount, which may provide a better orientation for the scope to treat a target site. In particular, the scope rolls 180 degrees to reorient the working channel.

However, any amount of roll can be implemented, which can be predetermined or otherwise. A scope roll can be initiated in a variety of manners, such as by receiving user input via an I/O device/component (via a user interface or otherwise), automatically determining to roll a scope, and so on.

In these examples, a user interface 402/502 provides information to assist a user in controlling a scope 404/504 and/or an instrument deployed through the scope 404/504, such as to perform a medical procedure. The user interface 402/502 can provide an image representation 406/506 representing a view from a perspective of the scope 404/504 and a working channel indicator 408/508 indicating an angle of rotation of a working channel of the scope 404/504 relative to the image representation 406/506. The working channel indicator 408/508 can be displayed in the user interface 402/502 when a working channel roll is implemented, constantly, and/or at another time. The image representation 406/506 can include, be based on, and/or generated from image data captured by an imaging device associated with the scope 404/504. Here, the image representation 406/506 depicts a kidney stone 410/510 and a cavity 412/512 adjacent to the kidney stone 410/510, which may typically be viewed when performing a procedure to remove the kidney stone 410/510 (although the kidney stone 410/510 may be oriented in other manners). As shown, the user interface 402/502 can include a user interface element 414/514 to cause the working channel of the scope 404/504 to roll (i.e., the scope 404/504 to roll). Meanwhile, an image 416/516 and element 418/518 of each figure depicts an orientation of the scope 404/504 within the anatomy of the patient for the respective figure. The element 418/518 represents an orientation of a tip and coordinate frame of the scope 404/504 for the respective image 416/516.

In general, an orientation of an image representation within a user interface can be correlated to an orientation of a tip/imaging device of a scope (with or without an offset). In other words, a frame of reference of the user (also referred to as "the user's view") via the user interface is correlated to an orientation of a tip/imaging device of the scope. As such, when the scope 404 rolls, the image representation generally rotates within the user interface unless a rotation adjustment is applied. To illustrate, in the context of FIGS. 4-1 through 4-9, a coordinate frame for the scope 404 can be initially oriented in the manner shown at 418 in FIG. 4-1, wherein an up direction of movement relative to the coordinate frame of the scope 404 (e.g., direction the arrow points for 418) corresponds to the left direction in FIG. 4-1. Here, a coordinate frame for the imaging device of the scope 404 is the same; although it may be offset in some cases. In this example, the user interface 402 provides the image representation 406 associated with the scope 404 with an offset in FIG. 4-1, such that the up direction in the user interface 402 corresponds to the right direction in the coordinate frame of the scope 404. Such offset can be maintained until a rotation adjustment is applied.

Further, control of a scope can generally be correlated to a user interface, so that the scope can be controlled by the user in an intuitive manner. For example, assume that the user provides input via an I/O component(s) to move the scope in an upward direction relative to the I/O component(s), such as by selecting an up control on the I/O component(s). Information regarding an orientation/position of the scope and/or an orientation of the image representation within the user interface can be used to move the scope in an upward direction on the user interface, even if such direction is not an upward direction relative to the coordinate frame of the scope. As such, the user can view the scope as moving in an upward direction on the user interface.

As noted above, FIGS. 4-1 through 4-9 illustrate an example of applying a rotation adjustment to the image representation 406 after the scope 404 has completed the roll. In these figures, the arrow next to the image 416 indicates a direction of roll of the scope 404, while the arrow next to the user interface 402 indicates a direction of rotation of the image representation 406 within the user interface 402. For example, in FIGS. 4-6 through 4-9, the arrow next to the user interface 402 indicates that the image representation 406 is rotating in a counterclockwise manner within the user interface 402, which is due a rotation adjustment applied to adjust/correct the orientation of the image representation 406.

As shown, FIG. 4-1 illustrates the image representation 402 and the working channel indicator 404 within the user interface 402 when the scope 404 is oriented at an initial position. Here, the scope 404 is oriented in the manner shown at 418. In this example, the user causes the scope 404 to roll by a predetermined amount by selecting the interface element 414. As shown in FIGS. 4-2 through 4-5, the scope 404 rolls in a counterclockwise manner by 180 degrees. However, the scope 404 can roll in a clockwise manner to achieve the same amount of roll. FIG. 4-5 illustrates the user interface 402 and the orientation of the scope 404 once the scope 404 has completed the roll. As the scope 404 rolls, the content within the image representation 406 rotates within the user interface 402 in a clockwise manner, as also shown in FIGS. 4-2 through 4-5. That is, a virtual horizon associated with the image representation 406 can rotate in a clockwise manner due to the roll of the scope 404 (and the associated imaging device of the scope 404). The virtual horizon can represent a reference line for content in the image representation 406 (e.g., a reference horizon for the anatomy of the patient). In the context of FIGS. 4-1 through 4-9, the virtual horizon can initially be a horizontal line in FIG. 4-1.

While the scope 404 rolls, the image representation 406 can be displayed in a cropped form. For example, as shown in FIGS. 4-2 through 4-5, the image representation 406 can be displayed in a circular form within the user interface 402. This can avoid presenting black bands in the user interface 402 due to missing image data from the imaging device. The cropped form can also indicate to the user that the scope 404 is rolling. Although many examples are discussed in the context of presenting the image representation 406 in a cropped manner (e.g., a circle) during and the roll of the scope 404, the image representation 406 can be displayed in a non-cropped manner and/or in other forms during the roll, such as an initial/original form of the image representation 406 (based on a field-of-view of the imaging device), another shape, and so on.

As the scope 404 rolls, the working channel indicator 408 can maintain the angle of rotation of the working channel relative to the image representation 406. In particular, as illustrated in FIGS. 4-2 through 4-5, the working channel indicator 408 remains stationary within the user interface 402 as the virtual horizon within the image representation 406 rotates to accurately indicate a position of the working channel relative to the content of the image representation 406. That is, the working channel indicator 408 can maintain the same angle of rotation within the user interface 402 as the scope 404 rolls from an initial orientation to 180 degrees. In this example, the working channel indicator 408 is presented in an overlaid manner over the image representation 406 as a partially transparent interface element. This can allow the image representation 406 to be at least partially viewed through the working channel indicator 408. However, the working channel indicator 408 can be displayed in other manners, such as in a non-overlaid manner with respect to 406, as a non-transparent interface element (e.g., solid), completely transparent interface element, and/or in other forms/manners.

When the scope 404 has completed the roll, and consequently, the working channel is rotated 180 degrees, a rotation adjustment can be applied to adjust/correct the orientation of the image representation 406. In examples, a determination can be made that the scope 404 completed the roll based on one or more of the techniques discussed herein (e.g., localization techniques). As shown in FIGS. 4-6 through 4-9, the rotation adjustment can include rotating the image representation 406 in a counterclockwise manner within the user interface 402, until the virtual horizon associated with the image representation 406 is returned to the initial orientation shown in FIG. 4-1 (e.g., the content within the image representation 406 is returned to the initial orientation). The image representation 406 can rotate by the same amount that the scope 404 rolled (e.g., 180 degrees). The image representation 406 can rotate within the user interface 402 while the scope 404 remains in the same orientation (e.g., the rolled/flipped position). FIG. 4-9 illustrates the user interface 402 (and the working channel indicator 408) when the image representation 406 has rotated 180 degrees to return the virtual horizon to the initial orientation. Although the rotation adjustment is discussed in the context of rotating the image representation 406 in a counterclockwise manner, the rotation adjustment can alternatively be implemented by rotating the image representation 406 in a clockwise manner.

While rotating the image representation 406, the image representation 406 can be displayed in a cropped form, in a similar manner as that discussed when rolling the scope 404. Once the rotation adjustment has been applied to the image representation 406 and the working channel 408 is rotated, as shown in FIG. 4-9, the image representation 406 can be returned to a non-cropped form. However, the image representation 406 can be displayed in other forms during and/or upon completing the scope roll. As such, the rotation adjustment can provide the user with the same frame of reference before and after rolling the scope 404 (e.g., the same virtual horizon), while allowing the user to accurately view the position of the working channel (e.g., that the working channel has been flipped).

As also shown in FIGS. 4-6 through 4-9, during the rotation adjustment of the image representation 406, the working channel indicator 408 can rotate within the user interface 402 in a counterclockwise manner to maintain an accurate representation of an angle of the working channel relative to the image representation 406. The working channel indicator 408 can rotate by the same amount the scope 404 rolled (e.g., 180 degrees).

In some embodiments, the rotation adjustment techniques discussed in the context of FIGS. 4-6 through 4-9 are implemented in cases where it may be difficult to accurately track an orientation of a tip of the scope 404 during the roll. For example, rolling the scope 404 can include disengaging/engaging a mechanical component of the scope 404/robotic arm, evaluating a tightness of an elongate shaft of the scope 404, sending one or more control signals to a component of a robotic system, and so on. Such operations can take an unknown amount of time and/or be associated with some amount of delay. Further, in examples where an operation(s) is performed at proximal end of the scope 404, such operation(s) may not instantaneously translate into roll at a distal end of the scope 404. Moreover, in some examples, the scope 404 can be rolled when an EM field generator is not being used, causing a control system to rely on data other than EM sensor data to track the roll of the scope 404, which can be less accurate/reliable.

Although FIGS. 4-1 through 4-9 are discussed in the context of the image representation 406 rotating when the scope 404 has completed the roll, the image representation 406 can rotate when other events occurs. For example, the image representation 406 can rotate in an incremental manner where the image representation 406 rotates a predetermined amount each time the scope 404 completes such amount of rotation (e.g., rotate 15 degrees for each 15 degree roll that is completed by the scope 404).

Meanwhile, FIGS. 5-1 through 5-5 illustrate an example of applying a rotation adjustment in a continuous approach while the scope 504 rolls. In these figures, the arrow next to the image 516 indicates a direction of roll of the scope 504. Here, the image representation 506 is continuously updated within the user interface 502 as the scope 504 rolls from an initial orientation to a final orientation at 180 degrees. As shown, a virtual horizon for the image representation 506 remains the same throughout the roll of the scope 504, while the working channel indicator 508 rotates around the image representation 506. In particular, the scope 504 rolls in a counterclockwise direction relative to a coordinate frame for the scope 504, and the working channel indicator 508 rotates in the same direction (i.e., a counterclockwise direction) relative to the user interface 502. Further, the image representation 506 can rotate in a counterclockwise direction in an unperceived manner. To make such adjustments to the working channel indicator 508 and the image representation 506, an orientation of the scope 504 can be tracked in real-time using one or more of the localization techniques discussed herein. This can allow the user interface 502 to present information in an accurate manner. As similarly discussed above, while the scope 504 rolls, the image representation 506 can be displayed in a cropped form, as shown in FIGS. 5-2 through 5-4. When the scope 504 has completed the roll, as shown in FIG. 5-5, the image representation 506 can return to a non-cropped form. By implementing such rotation adjustment in a continuous manner, the user may perceive the image representation 506 as remaining the same, which may further assist in avoiding the user from becoming disoriented within the anatomy of the patient. That is, in FIGS. 5-1 through 5-5, the orientation of the image representation 506 can be updated in a continuous manner to maintain a virtual horizon for the anatomy of the patient (e.g., maintain the user's frame of reference).

Although various image representations are depicted in FIGS. 4-1 through 4-9 and FIGS. 5-1 through 5-9 in a cropped or non-cropped form during particular phases of a scope roll, an image representation can be displayed in a cropped or non-cropped form at any time before, during, and/or after a scope roll.

Example User Interface

FIG. 6 illustrates an example user interface 602 to assist a user in controlling a scope and/or an instrument deployed through a working channel of the scope in accordance with one or more embodiments. The user interface 602 can provide an image representation 604 representing a view from a perspective of the scope and a working channel indicator 606 indicating an angle of rotation of a working channel of the scope relative to the image representation 604. The image representation 604 can include, be based on, and/or generated from image data captured by an imaging device associated with the scope. Here, the image representation 604 depicts a kidney stone 608 and a cavity 610 adjacent to the kidney stone 608. In this example, the user interface 602 is presented during a medical procedure. However, the user interface 602 can be presented at other times.

As shown, the user interface 602 can include a working channel element 612 to cause the working channel of the scope to rotate. The working channel indicator 606 can be implemented as a semi-transparent semi-circular element that is overlaid on the image representation 604; however, the working channel element 612 can take other forms and/or be positioned at other locations within the user interface 602. In one example, a user can select the working channel element 612 to cause the scope to roll 180 degrees (e.g., to flip from an initial orientation to an orientation that is rotated 180 degrees); although rotations are also possible. In another example, a user can provide first input via an I/O component (e.g., the user interface 602, a controller, etc.) to initiate a scope roll and provide second input to stop the scope roll. In yet another example, a user can provide input to roll the scope by selecting and holding a control element on an I/O component, causing the scope to roll while the control element is selected. In any event, one or more of the rotation adjustment techniques discussed herein can be implemented to adjust the image representation 604 when/after the scope rolls. Further, the working channel indicator 606 can be adjusted to indicate an orientation of the working channel of the scope. The user interface 602 can also include a horizon roll element 614 to cause the scope to roll without applying a rotation adjustment to the image representation 604 in the user interface 602 (e.g., without roll correcting the scope image). This can be used to align the visual horizon with the kidney's main plane or other features. This can also be used to align a primary/principal plane of articulation of the scope, so that the scope can reach/navigate more easily in a location.

Further, the user interface 602 can include articulation bars 616, 618 around the image representation 604 to view an amount of articulation associated with a selected instrument (e.g., the scope or tool, in this example). The top/bottom articulation bar 616 can indicate an amount of vertical articulation. For example, the top/bottom articulation bar 616 can be positioned above or below the image 604 and/or expand/contract in length to indicate vertical articulation of the instrument. In the example of FIG. 6, the top/bottom articulation bar 616 is positioned above the image representation 604 to indicate that the scope is articulated up. The right/left articulation bar 618 can indicate an amount of horizontal articulation. For example, the right/left articulation bar 618 can be positioned to the right or left of the image representation 604 and/or expand/contract in length to indicate horizontal articulation of the instrument. In the example of FIG. 6, the right/left articulation bar 618 is positioned to the right of the image representation 604 to indicate that the scope is articulated to the right.

The user interface 602 can also include interface elements 620, 622 to select an instrument to control. The interface element 620 enables control of the scope, and the interface element 622 enables control of an instrument associated with the scope (also referred to as a "tool"). The instrument associated with the scope can be deployed through a working channel of the scope. In this example, the scope is selected, which enables the user to navigate the scope and causes the user interface 602 to display information regarding the scope.

Example Flow Diagram

Figures 4, 5, 6, 7, 8, 9:
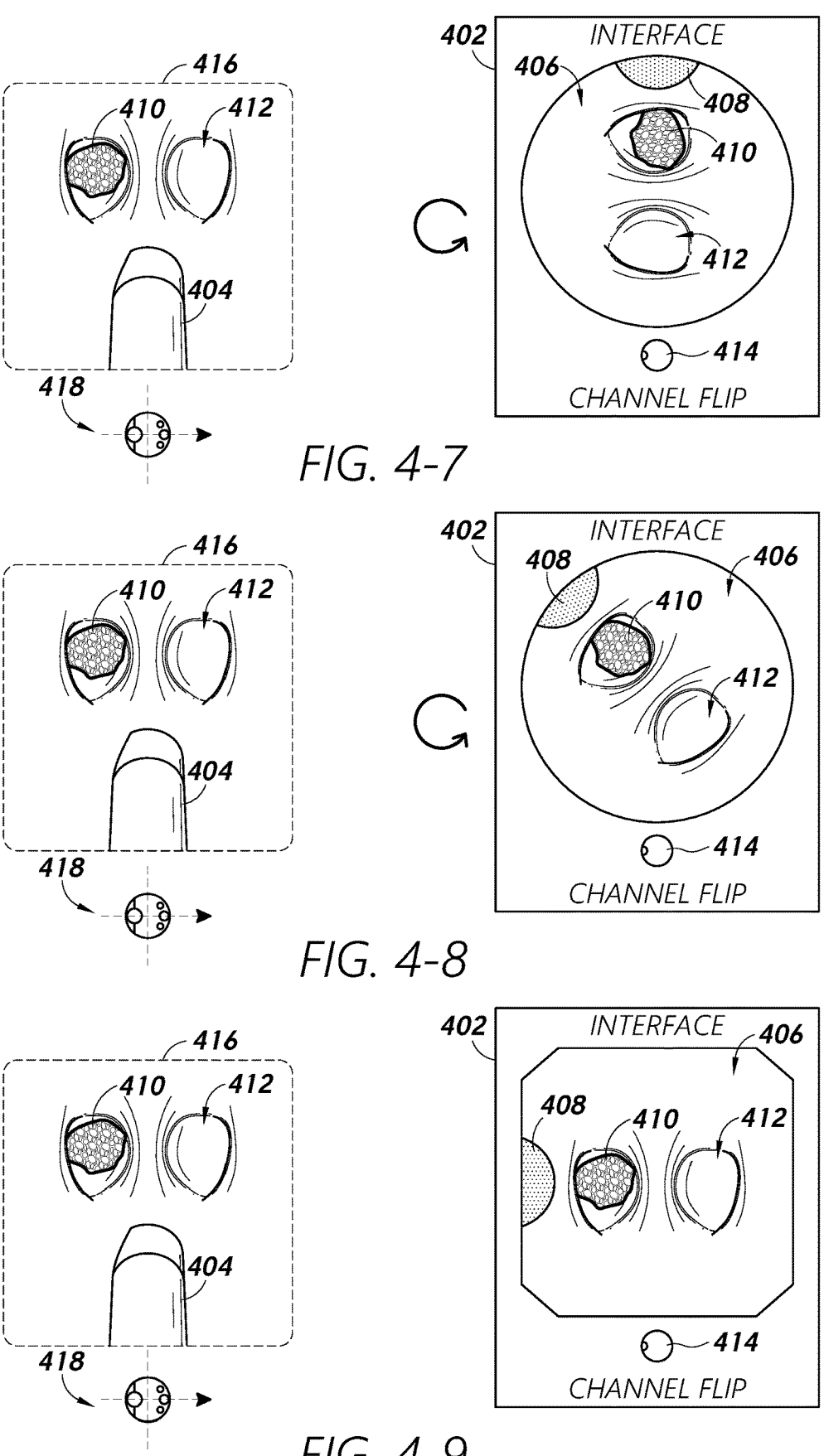
Figures 1, 2, 3, 5:
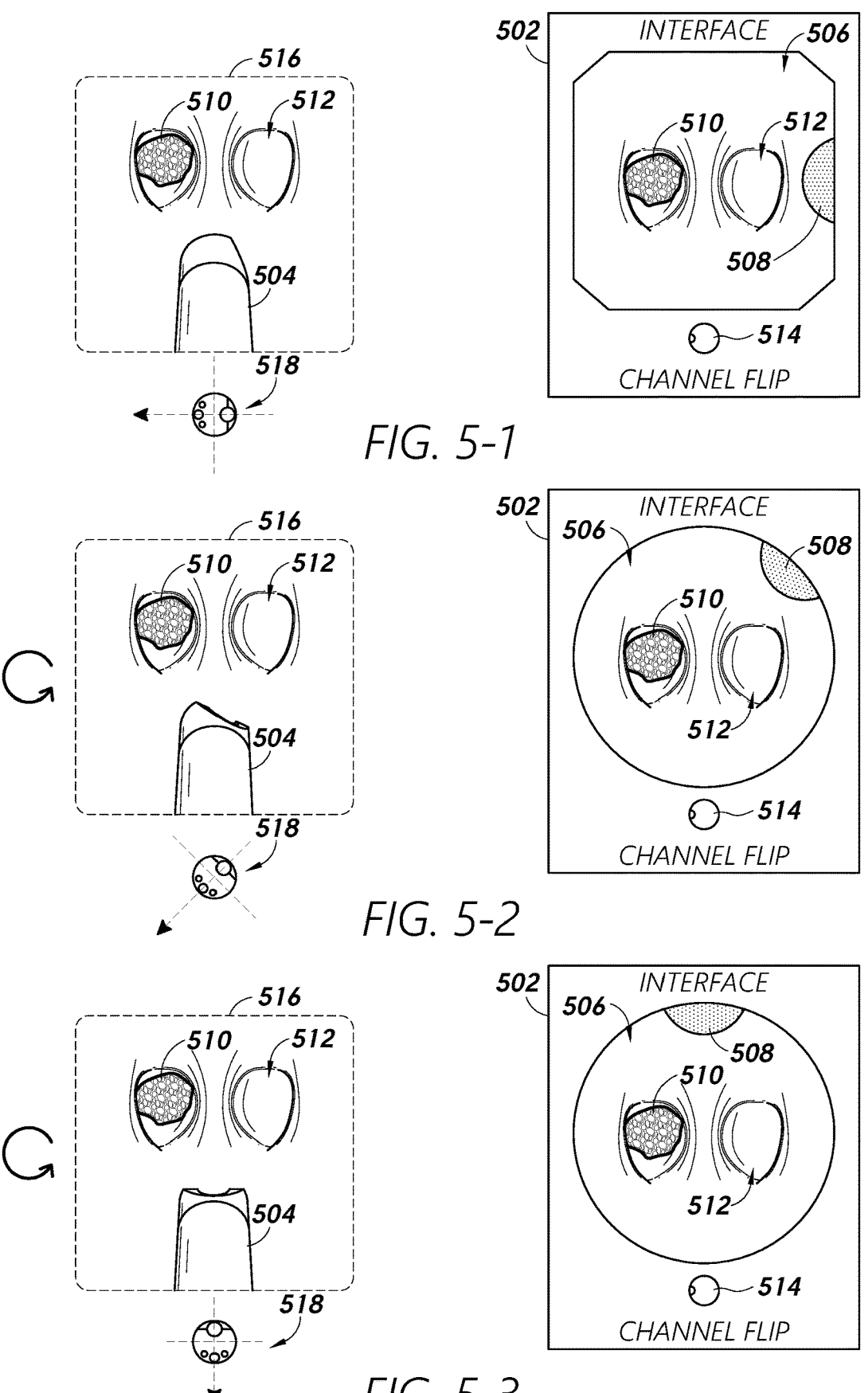
Figures 4, 5:
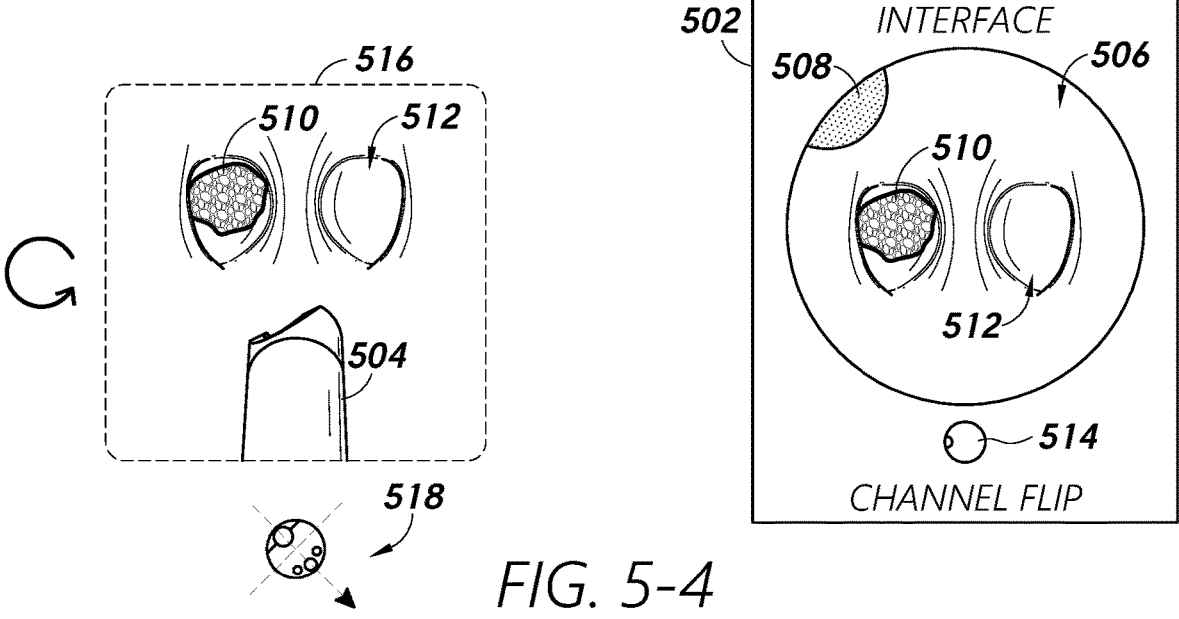
Figure 5:
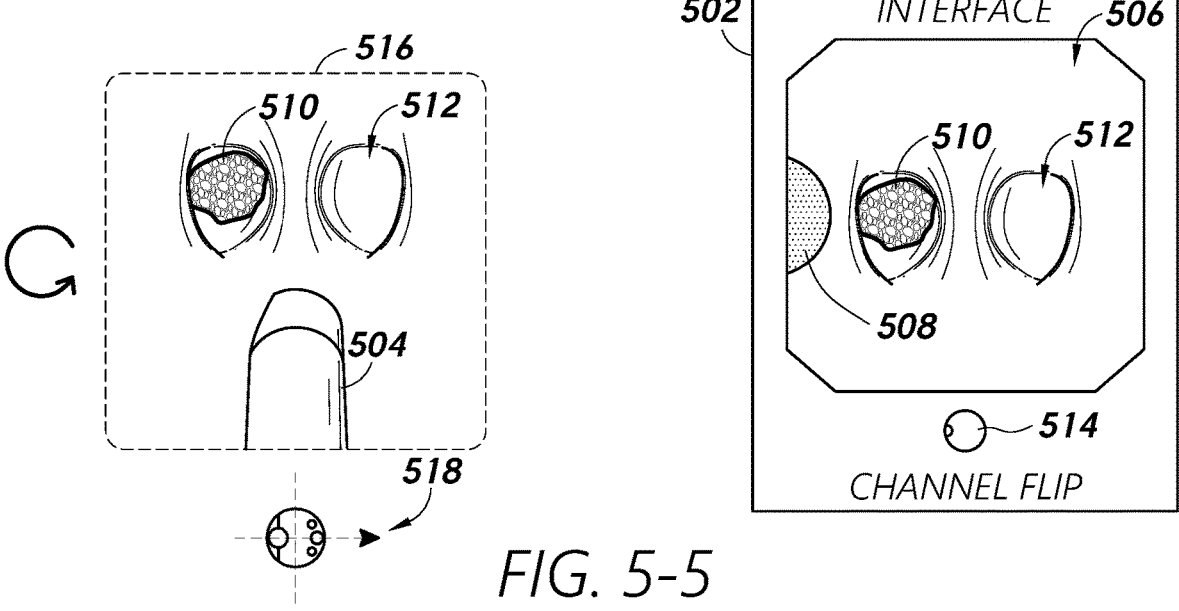
Figure 6:
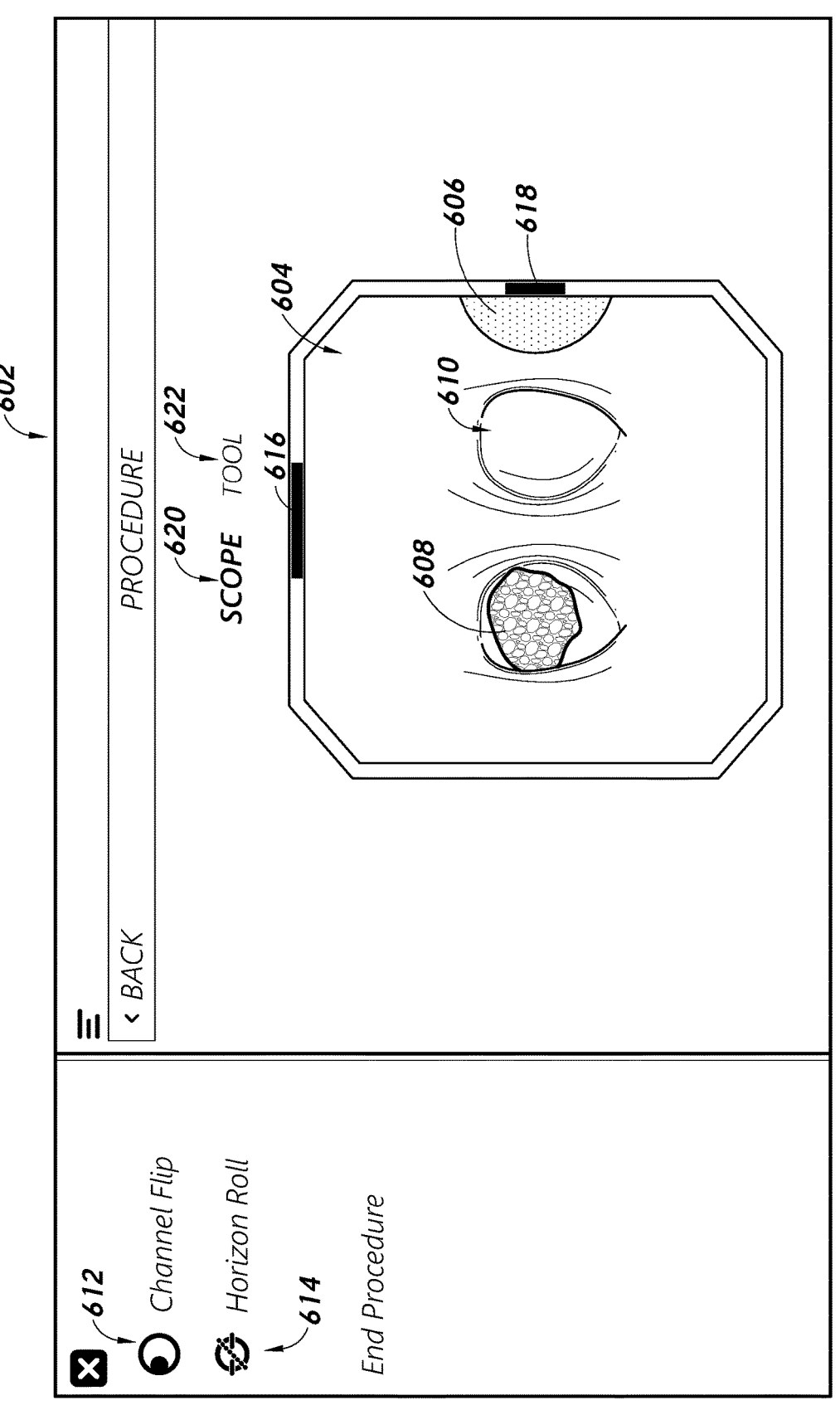

FIG. 7 illustrates an example flow diagram of a process 700 for applying a rotation adjustment to a scope view within a user interface in accordance with one or more embodiments. The various operations/acts associated with the process 700 can be performed by control circuitry implemented in any of the devices/systems discussed herein or a combination thereof, such as the control system 150, the robotic system 110, the table 170, a medical instrument, and/or another device. Although various blocks are illustrated as being part of the process 700, any of such blocks can be eliminated. Further, additional blocks can be implemented as part of the process 700. The order in which the blocks are illustrated is provided merely for illustrative purposes, and the blocks can be implemented in any order. In some embodiments, one or more of the blocks of the process 700 are implemented as executable instructions, that when executed by control circuitry, cause the control circuitry to perform the functionality/operations discussed. However, one or more of the blocks of the process 700 can be implemented in other manners, such as by other devices/ systems, a user(s), etc.

At block 702, the process 700 can include receiving image data from an imaging device associated with a scope. The scope can include a working channel to deploy a medical instrument/tool. The working channel can offset from a longitudinal axis of the scope. In some instances, the imaging device is disposed on an end of the scope, while in other instances the imaging device is deployed through the working channel of the scope. In examples, image data can be received in real-time, such as receiving multiple images from the imaging device.

At block 704, the process 700 can include generating an image representation based at least in part on the image data. For example, the image representation can include/represent the image data from the scope. In some cases, the image data is reformatted/converted to generate the image representation.

At block 706, the process 700 can include causing the image representation to be displayed in a user interface. In one example, causing the image data to be displayed can include sending data to a display so that the display can present the image representation via the user interface. In another example, causing the image representation to be displayed can including displaying/presenting the image representation via a display.

At block 708, the process 700 can include causing a working channel indicator to be displayed. The working channel indicator can indicate an angle of rotation of the working channel relative to the image representation. In one example, causing the working channel indicator to be displayed can include sending data to a display so that the display can present the image representation via the user interface. In another example, causing the image representation to be displayed can including displaying/presenting the working channel indicator via a display. In some instances, the working channel indicator is overlaid on the image representation and/or positioned at a perimeter of the image representation.

At block 710, the process 700 can include receiving, from an input device, an input control signal to rotate the working channel. For example, a user can use the input device to provide input to roll the scope and the input device can generate/send the input signal indicating to roll the scope. In some cases, the input is to roll the scope/working channel by a predetermined amount.

At block 712, the process 700 can include controlling the scope to roll based at least in part on the input control signal. For example, a control signal can be sent to a robotic system/robotic arm to control the robotic arm to roll the scope, which can be in particular rotation direction. In some cases, the scope can be controlled to roll a predetermined amount, such as to flip a working channel from one orientation to another orientation.

At block 714, the process 700 can include determining that the scope has completed the roll. Such determination can be based on feedback data from a robotic arm configured to couple to the scope, sensor data generated by a position sensor associated with the scope, and/or a control signal generated to control a robotic arm. In some instances, the roll of the scope is tracked over time.

At block 718, the process 700 can include determining an amount that the scope has rolled. Such determination can be based on feedback data from a robotic arm configured to couple to the scope, sensor data generated by a position sensor associated with the scope, and/or a control signal generated to control a robotic arm. Although the process 700 illustrates blocks 714 and 716, in some cases one or more of such blocks (and/or other blocks of the process 700) are not implemented.

At block 718, the process 700 can include causing the working channel indicator to rotate within the user interface. For example, based at least in part on the amount that the scope has rolled, the working channel indicator can rotate from a first orientation relative to the user interface to a second orientation relative to the user interface. The first orientation can indicate a first angle of rotation of the working channel and the second orientation can indicate a second angle of rotation of the working channel.

At block 720, the process 700 can include applying a rotation adjustment to the image representation in the user interface. For example, based at least in part on the amount that the scope has rolled, the image representation can rotate within the user interface. In some instances, the image representation can rotate within the user interface in response to determining that the scope has completed the roll. In other instances, the image representation can rotate as the scope rolls, such as in a continuous manner based on a current orientation of the scope. Here, the image representation can rotate without being perceived by a user via the user interface. In examples, the image representation can be displayed in a cropped form while the scope rolls and/or while the image representation rotates. Further, in examples, the image representation can rotate within the user interface in a same rotation direction (e.g., clockwise or counterclockwise) as the scope rolls relative to a frame of reference of the tip of the scope (e.g., a coordinate frame of the scope).

Additional Embodiments

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is understood with the context as used in general to convey that an item, term, element, etc. may be either X, Y, or Z. Thus, such conjunctive language is not generally intended to imply that certain embodiments require at least one of X, at least one of Y, and at least one of Z to each be present.

It should be appreciated that in the above description of embodiments, various features are sometimes grouped together in a single embodiment, figure, or description thereof for the purpose of streamlining the disclosure and aiding in the understanding of one or more of the various aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the disclosure herein disclosed and claimed below should not be limited by the particular embodiments described above, but should be determined by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example embodiments belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:

1. A control system comprising:

a communication interface configured to receive image data from an imaging device associated with a scope that includes a working channel to deploy a medical instrument; and control circuitry communicatively coupled to the communication interface and configured to:

generate an image representation of the image data;

display the image representation in a user interface;

display a working channel indicator in the user interface, the working channel indicator indicating an angle of rotation of the working channel relative to the image representation;

determine an amount that the scope has rolled;

rotate the working channel indicator within the user interface based at least in part on the amount that the scope has rolled;

rotate the image data in the opposite direction of the scope roll so that an orientation of the image representation remains fixed relative to the user interface while the scope rolls and the working channel indicator rotates; and selectively crop the image representation in the user interface based on whether the scope is rolling, the selective cropping including:

displaying the image representation in a cropped form while the scope is rolling; and displaying the image representation in a non-cropped form while the scope is not rolling.

2. The control system of claim 1, wherein rotating the working channel indicator includes:

causing the working channel indicator to rotate within the user interface from a first orientation relative to the user interface to a second orientation relative to the user interface.

3. The control system of claim 2, wherein the control circuitry is configured to display the working channel indicator by overlaying the working channel indicator on the image representation.

4. The control system of claim 1, wherein the control circuitry is configured to:

determine that the amount that the scope has rolled has reached a predetermined angle of rotation; and in response to determining that the amount that the scope has rolled has reached the predetermined angle of rotation, cause the image representation to rotate within the user interface.

5. The control system of claim 1, wherein rotating the image data includes rotating the image data in the opposite direction of the scope roll in a continuous manner as the scope rolls.

6. The control system of claim 1, wherein the control circuitry is configured to determine the amount that the scope has rolled based on at least one of feedback data from a robotic arm configured to couple to the scope, sensor data generated by a position sensor associated with the scope, or a control signal generated to control the robotic arm.

7. The control system of claim 1, wherein the control circuitry is configured to:

receive, from an input device, an input control signal to rotate the working channel; and control the scope to roll a predetermined amount based at least in part on the input control signal.

8. The control system of claim 7, wherein the control circuitry is configured to control the scope to roll by controlling the scope to roll a predetermined amount.

9. The control system of claim 1, wherein the control circuitry is further configured to:

determine that the scope has stopped rolling, wherein the image representation is displayed in the non-cropped form responsive to determining that the scope has stopped rolling.

10. A method comprising:

receiving image data from an imaging device associated with a scope, the scope including a working channel;

displaying, by control circuitry, an image representation of the image data in a user interface;

displaying, by the control circuitry, a working channel indicator in the user interface, the working channel indicator indicating an angle of rotation of the working channel relative to the image representation;

determining an amount that the scope has rolled;

rotating the working channel indicator within the user interface based at least in part on the amount that the scope has rolled;

rotating the image data in the opposite direction of the scope roll so that an orientation of the image representation remains fixed relative to the user interface while the scope rolls and the working channel indicator rotates; and selectively cropping the image representation in the user interface based on whether the scope is rolling, the selective cropping including:

displaying the image representation in a cropped form while the scope is rolling; and displaying the image representation in a non-cropped form while the scope is not rolling.

11. The method of claim 10, further comprising:

determining that the amount that the scope has rolled has reached a predetermined angle of rotation, wherein the rotating the image representation and the rotating the working channel indicator occurs in response to the determining that the amount that the scope has rolled has reached the predetermined angle of rotation.

12. The method of claim 10, wherein;

rotating the image data includes rotating the image data in the opposite direction of the scope roll in a continuous manner as the scope rolls; and the determining the amount that the scope has rolled is based on at least one of feedback data from a robotic arm configured to couple to the scope, position data generated by a position sensor associated with the scope, or a control signal generated to control the robotic arm.

13. The method of claim 10, further comprising:

receiving, from an input device, user input to rotate the scope by a predetermined amount; and controlling the scope to roll the predetermined amount.

14. The method of claim 10, wherein the displaying the working channel indicator includes overlaying the working channel indicator on the image representation.

15. A system comprising:

a scope that includes a working channel to removably receive a medical instrument;

an imaging device configured to couple to the scope; and control circuitry communicatively coupled to the scope and the imaging device, the control circuitry being configured to:

receive image data from the imaging device;

cause an image representation of the image data to be displayed in a user interface;

cause a working channel indicator to be displayed in the user interface, the working channel indicator indicating an angle of rotation of the working channel;

determine an amount that the scope has rolled;

based at least in part on the amount that the scope has rolled, rotate the working channel indicator in the user interface;

rotate the image data in the opposite direction of the scope roll so that an orientation of the image representation remains fixed relative to the user interface while the scope rolls and the working channel indicator rotates; and selectively crop the image representation in the user interface based on whether the scope is rolling, the selective cropping including:

displaying the image representation in a cropped form while the scope is rolling; and displaying the image representation in a non-cropped form while the scope is not rolling.

16. The system of claim 15, wherein the working channel is offset from a longitudinal axis of the scope.

17. The system of claim 15, wherein the control circuitry is configured to:

control the scope to roll in a rotation direction, wherein rotating the image data in the opposite direction of the scope roll causes the image representation to rotate within the user interface in the rotation direction.

18. The system of claim 15, wherein the control circuitry is further configured to:

determine that the amount that the scope has rolled has reached a predetermined angle of rotation, wherein, in response to determining that the amount that the scope has rolled has reached the predetermined angle of rotation, causing the image representation to rotate within the user interface.

19. The system of claim 15, wherein the control circuitry is configured to rotate the image data in a continuous manner as the scope rolls.

* * * * *